US009861347B2

United States Patent
Chin-Chen et al.

(10) Patent No.: US 9,861,347 B2
(45) Date of Patent: Jan. 9, 2018

(54) PATENT FORAMEN OVALE CLOSURE METHOD

(75) Inventors: Chao Chin-Chen, Edison, NJ (US); Randy David B. Grishaber, Danville, CA (US); Gene W. Kammerer, East Brunswick, NJ (US); Isaac John Khan, Bridgewater, NJ (US); Jin Park, Parsippany, NJ (US)

(73) Assignee: CORDIS CORPORATION, Milpitas, CA (US)

( * ) Notice: Subject to any disclaimer, the term of this patent is extended or adjusted under 35 U.S.C. 154(b) by 863 days.

(21) Appl. No.: 13/434,266

(22) Filed: Mar. 29, 2012

(65) Prior Publication Data

US 2012/0197292 A1 Aug. 2, 2012

Related U.S. Application Data

(63) Continuation of application No. 11/469,653, filed on Sep. 1, 2006, now abandoned.

(Continued)

(51) Int. Cl.
*A61B 17/08* (2006.01)
*A61B 17/00* (2006.01)
(Continued)

(52) U.S. Cl.
CPC ...... *A61B 17/0057* (2013.01); *A61B 17/0401* (2013.01); *A61B 17/08* (2013.01); *A61B 17/0467* (2013.01); *A61B 2017/00022* (2013.01); *A61B 2017/00575* (2013.01); *A61B 2017/00592* (2013.01);
(Continued)

(58) Field of Classification Search
CPC ............ A61B 17/0057; A61B 17/0401; A61B 2090/064; A61B 2017/00022; A61B 2017/00592; A61B 2017/00619; A61B 2017/0417; A61B 2017/0496; A61B 17/08; A61B 17/0467; A61B 2017/00575;
(Continued)

(56) References Cited

U.S. PATENT DOCUMENTS 3,874,388 A 4/1975 King et al.
4,917,089 A 4/1990 Sideris
(Continued)

FOREIGN PATENT DOCUMENTS

WO  WO 03/022160 A1  3/2003
WO  WO 03/094742 A1  11/2003
(Continued)

OTHER PUBLICATIONS

Shah, Sandy Do, "Patent Foramen Ovale", Copyright 2003, eMedicine.com, Inc. Http://emedicine.com/med/topic1766.htm.
(Continued)

*Primary Examiner* — Jing Ou
(74) *Attorney, Agent, or Firm* — Khoi Q. Ta

(57) ABSTRACT

The present invention relates to devices for closing a passageway in a body, for example a patent foramen ovale (PFO) in a heart, and related methods of using such closure devices for closing the passageway. The method includes introducing a mechanical closure device into an atrium of the heart and transeptally deploying the closure device across the interatrial septum to provide proximation of the septum secundum and septum primum.

10 Claims, 30 Drawing Sheets

Related U.S. Application Data

(60) Provisional application No. 60/713,388, filed on Sep. 1, 2005.

(51) Int. Cl.
*A61B 17/04* (2006.01)
*A61B 17/06* (2006.01)
*A61B 90/00* (2016.01)

(52) U.S. Cl.
CPC ............... *A61B 2017/00606* (2013.01); *A61B 2017/00619* (2013.01); *A61B 2017/00867* (2013.01); *A61B 2017/0417* (2013.01); *A61B 2017/0419* (2013.01); *A61B 2017/0496* (2013.01); *A61B 2017/06052* (2013.01); *A61B 2090/064* (2016.02)

(58) Field of Classification Search
CPC  A61B 2017/00606; A61B 2017/00867; A61B 2017/0419; A61B 2017/06052
USPC ................ 606/213, 215, 216, 151, 155, 157
See application file for complete search history.

(56) References Cited

U.S. PATENT DOCUMENTS

| | | | |
|---|---|---|---|
| 5,171,259 A | 12/1992 | Inoue | |
| 5,284,488 A | 2/1994 | Sideris | |
| 5,433,727 A | 7/1995 | Sideris | |
| 6,080,182 A | 6/2000 | Shaw et al. | |
| 6,171,329 B1 | 1/2001 | Shaw et al. | |
| 6,436,088 B2 | 8/2002 | Frazier et al. | |
| 6,508,828 B1 | 1/2003 | Akerfeldt et al. | |
| 6,616,684 B1 | 9/2003 | Vidlund et al. | |
| 6,623,508 B2 | 9/2003 | Shaw et al. | |
| 6,911,037 B2 | 6/2005 | Gainor et al. | |
| 6,913,614 B2 | 7/2005 | Marino et al. | |
| 7,220,265 B2 * | 5/2007 | Chanduszko et al. ........ 606/139 | |
| 8,114,123 B2 * | 2/2012 | Brenzel et al. ................ 606/213 | |
| 2002/0165574 A1 | 11/2002 | Ressemann et al. | |
| 2002/0165598 A1 | 11/2002 | Wahr et al. | |
| 2002/0183787 A1 | 12/2002 | Wahr et al. | |
| 2003/0050600 A1 | 3/2003 | Ressemann et al. | |
| 2003/0144694 A1 | 7/2003 | Chanduszko et al. | |
| 2003/0208232 A1 | 11/2003 | Blaeser et al. | |
| 2004/0127917 A1 | 7/2004 | Ginn | |
| 2004/0176799 A1 | 9/2004 | Chanduszko et al. | |
| 2004/0243122 A1 | 12/2004 | Auth et al. | |
| 2004/0267306 A1 | 12/2004 | Blaeser et al. | |
| 2005/0059984 A1 | 3/2005 | Chanduszko et al. | |
| 2005/0075665 A1 * | 4/2005 | Brenzel et al. ................ 606/213 | |
| 2005/0101984 A1 | 5/2005 | Chanduszko et al. | |
| 2005/0119675 A1 | 6/2005 | Adams et al. | |
| 2005/0125032 A1 | 6/2005 | Whisenant et al. | |
| 2005/0131447 A1 | 6/2005 | Wahr et al. | |
| 2005/0187568 A1 | 8/2005 | Klenk et al. | |
| 2005/0267523 A1 | 12/2005 | Devellian et al. | |
| 2005/0267526 A1 | 12/2005 | Wahr et al. | |
| 2005/0277983 A1 | 12/2005 | Saadat et al. | |
| 2006/0009800 A1 | 1/2006 | Christianson et al. | |
| 2006/0036282 A1 | 2/2006 | Wahr et al. | |
| 2006/0036584 A1 | 2/2006 | Isa | |
| 2007/0032796 A1 * | 2/2007 | Chin-Chen ........ A61B 17/0057 606/139 | |

FOREIGN PATENT DOCUMENTS

| | | |
|---|---|---|
| WO | WO 03/103476 A2 | 12/2003 |
| WO | WO 2004/026147 A2 | 4/2004 |

OTHER PUBLICATIONS

International Search Report and Written Opinion for Application No. PCT/US2006/034346, dated Jan. 17, 2007, 10 pages.

* cited by examiner

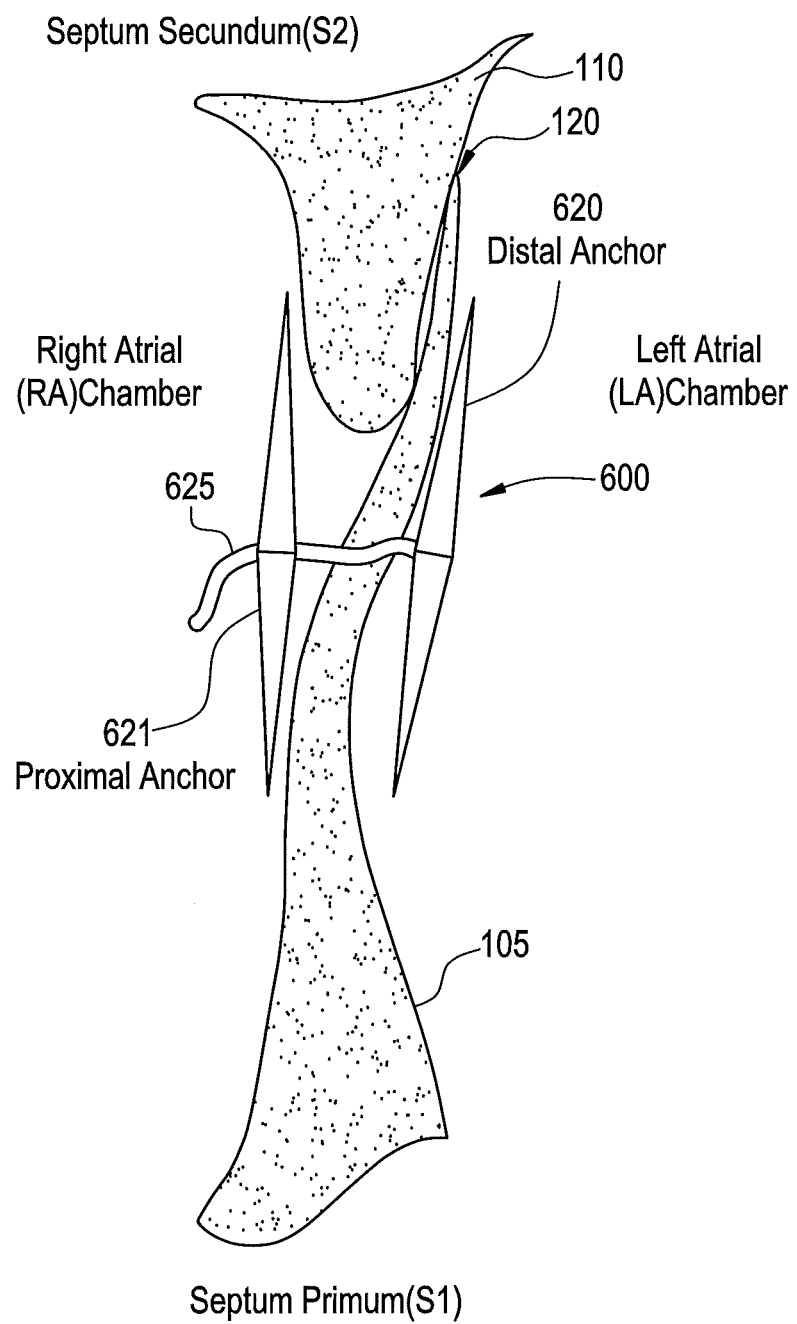

635
Shaped Catheter
(Deployment System)

PATENT FORAMEN OVALE CLOSURE METHOD

CROSS-REFERENCE TO RELATED APPLICATION

This application is a continuation of U.S. application Ser. No. 11/469,653 filed on Sep. 1, 2006, and claims priority thereto under 35 U.S.C. § 120, which application claims the benefit under 35 U.S.C. 119(e) to U.S. Provisional Application, Ser. No. 60/713,388, filed Sep. 1, 2005, which is incorporated by reference herein.

FIELD OF THE INVENTION

This invention relates to devices for closing a passageway in a body, for example a patent foramen ovale (PFO) in a heart, and related methods of using such closure devices for closing the passageway.

BACKGROUND OF THE INVENTION

Patent foramen ovale (PFO) is an anatomical interatrial communication with potential for right-to-left shunting of blood. Patent foramen ovale is a flap-like opening between the atrial septa primum and secundum at the location of the fossa ovalis that persists after age one year. In utero, the foramen ovale serves as a physiologic conduit for right-to-left shunting of blood in the fetal heart. After birth, with the establishment of pulmonary circulation, the increased left atrial blood flow and pressure presses the septum primum (SP) against the walls of the septum secundum (SS), covering the foramen ovale and resulting in functional closure of the foramen ovale. This closure is usually followed by anatomical closure of the foramen ovale due to fusion of the septum primum (SP) to the septum secundum (SS).

Where anatomical closure of the foramen ovale does not occur, a patent foramen ovale (PFO) is created. A patent foramen ovale is a persistent, usually flap-like opening between the atrial septum primum (SP) and septum secundum (SS) of a heart. A patent foramen ovale results when either partial or no fusion of the septum primum (SP) to the septum secundum (SS) occurs. In the case of partial fusion or no fusion, a persistent passageway (PFO track) exists between the septum primum (SP) and septum secundum (SS). This opening or passageway is typically parallel to the plane of the septum primum, and has a mouth that is generally oval in shape. Normally the opening is relatively long, but quite narrow. The opening may be held closed due to the mean pressure in the left atrium (LA) being typically higher than in the right atrium (RA). In this manner, the septum primum acts like a one-way valve, preventing fluid communication between the right and left atria through the PFO track. However, at times, the pressure may temporarily be higher in the right atrium, causing the PFO track to open up and allow some fluid to pass from the right atrium to the left atrium. Although the PFO track is often held closed, the endothelialized surfaces of the tissues forming the PFO track prevent the tissues from healing together and permanently closing the PFO track.

Studies have shown that a relatively large percentage of adults have a patent foramen ovale (PFO). It is believed that embolism via a PFO may be a cause of a significant number of ischemic strokes, particularly in relatively young patients. It has been estimated that in 50% of cryptogenic strokes, a PFO is present. Blood clots that form in the venous circulation (e.g., the legs) can embolize, and may enter the arterial circulation via the PFO, subsequently entering the cerebral circulation, resulting in an embolic stroke. Blood clots may also form in the vicinity of the PFO, and embolize into the arterial circulation and into the cerebral circulation. Patients suffering a cryptogenic stroke or a transient ischemic attack (TIA) in the presence of a PFO often are considered for medical therapy to reduce the risk of a recurrent embolic event.

Pharmacological therapy often includes oral anticoagulants or antiplatelet agents. These therapies may lead to certain side effects, including hemorrhage. If pharmacologic therapy is unsuitable, open heart surgery may be employed to close a PFO with stitches, for example. Like other open surgical treatments, this surgery is highly invasive, risky, requires general anesthesia, and may result in lengthy recuperation.

Nonsurgical closure of a PFO is possible with umbrella-like devices developed for percutaneous closure of atrial septal defects (ASD) (a condition where there is not a well-developed septum primum (SP)). Many of these conventional devices used for ASD, however, are technically complex, bulky, and difficult to deploy in a precise location. In addition, such devices may be difficult or impossible to retrieve and/or reposition should initial positioning not be satisfactory. Moreover, these devices are specially designed for ASD and therefore may not be suitable to close and seal a PFO, particularly because the septum primum (SP) overlaps the septum secundum (SS).

SUMMARY OF THE INVENTION

The present invention relates to a method of deploying a mechanical closure device through the septum of a heart to facilitate closing of a patent foramen ovale. The method comprises the steps of accessing a first atrium of the heart with a deployment device carrying the mechanical closure device. The mechanical closure device includes a proximal and distal anchor with a closure line attached there between. The deployment device is then advanced distally until the deployment device penetrates through the interatrial septum into the second atrium. A mechanical closure device is then introduced into the second atrium of the heart. The closure device is then transeptally deployed across the septum secundum and/or septum primum to provide proximation between the septum secundum and septum primum.

In another embodiment of the present invention, the method comprises the steps of accessing a first atrium of the heart with a deployment device carrying the mechanical closure device. The mechanical closure device includes a proximal and distal anchor with a closure line attached there between. The deployment device is then advanced distally until the deployment device penetrates through at least one appendage of the interatrial septum into the second atrium. A mechanical closure device is then introduced into the second atrium of the heart. The closure device is then transeptally deployed across the penetrated interatrial septum to provide proximation between the septum secundum and septum primum.

BRIEF DESCRIPTION OF THE DRAWINGS

FIG. 8C illustrates substantial closure of the PFO track with a single penetration through the septum primum according to one embodiment of the present invention.

DETAILED DESCRIPTION OF THE INVENTION

The various figures show embodiments of the patent foramen ovale (PFO) closure device and methods of using the device to close a PFO. The device and related methods are described herein in connection with mechanically closing a PFO. These devices, however, also are suitable for closing other openings or passageways, including other such openings in the heart, for example atrial septal defects, ventricular septal defects, and patent ducts arterioses, as well as openings or passageways in other portions of a body such as an arteriovenous fistula. The invention therefore is not limited to use of the inventive closure devices to close PFO's.

A human heart has four chambers. The upper chambers are called the left and right atria, and the lower chambers are called the left and right ventricles. A wall of muscle called the septum separates the left and right atria and the left and right ventricles. That portion of the septum that separates the two upper chambers (the right and left atria) of the heart is termed the atrial (or interatrial) septum while the portion of the septum that lies between the two lower chambers (the right and left ventricles) of the heart is called the ventricular (or interventricular) septum.

Figure 1:
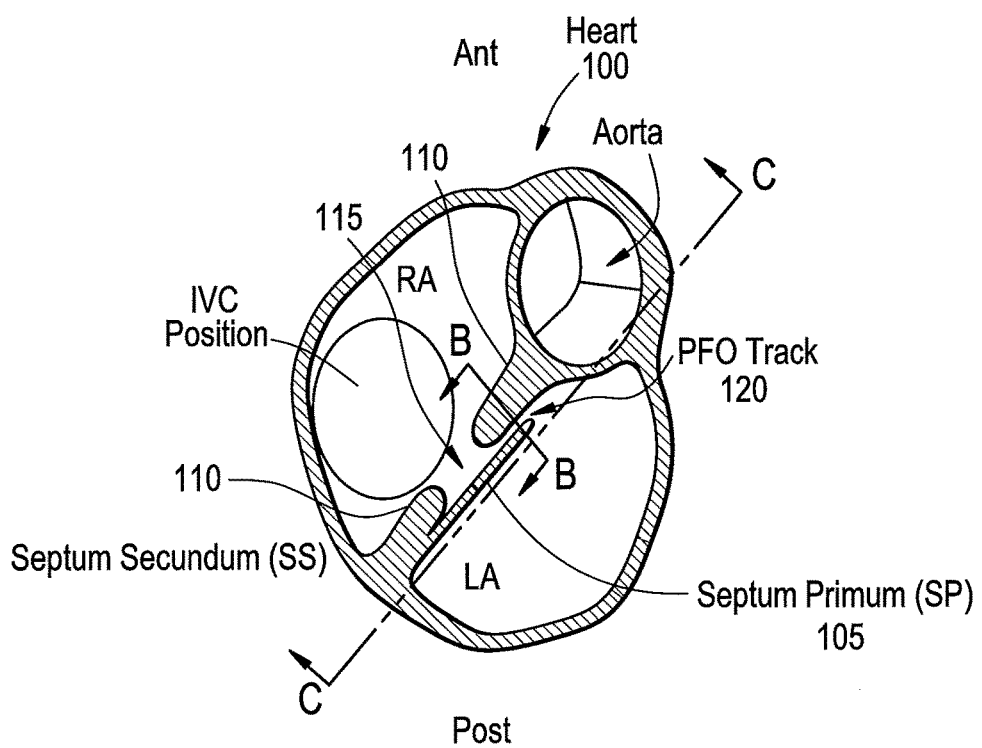
FIG. 1 is a short axis view of the heart at the level of the right atrium (RA) and the left atrium (LA), in a plane generally parallel to the atrio-ventricular groove, and at the level of the aortic valve, showing a PFO track.

FIG. 1 illustrates a short-axis view of the heart 100 at the level of the right atrium (RA) and left atrium (LA), in a plane generally parallel to the atrio-ventricular groove, and at the level of the aortic valve. This view is looking from caudal to cranial. FIG. 1 also shows the septum primum (SP) 105, a flap-like structure, which normally covers the foramen ovale 115, an opening in the septum secundum (SS) 110 of the heart 100. In utero, the foramen ovale 115 serves as a physiologic conduit for right-to-left shunting of blood in the fetal heart. After birth, with the establishment of pulmonary circulation, the increased left atrial blood flow and pressure presses the septum primum (SP) 105 against the walls of the septum secundum (SS) 110, covering the foramen ovale 115 and resulting in functional closure of the foramen ovale 115. This closure is usually followed by anatomical closure of the foramen ovale 115 due to fusion of the septum primum (SP) 105 to the septum secundum (SS) 110.

Figure 2:
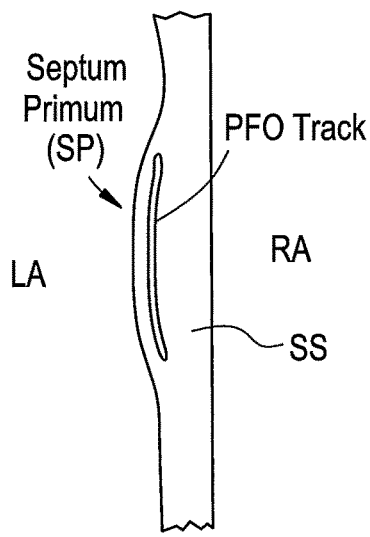
FIG. 2 is a cross-sectional view of the PFO track of FIG. 1 in a closed configuration.
Figure 4A:
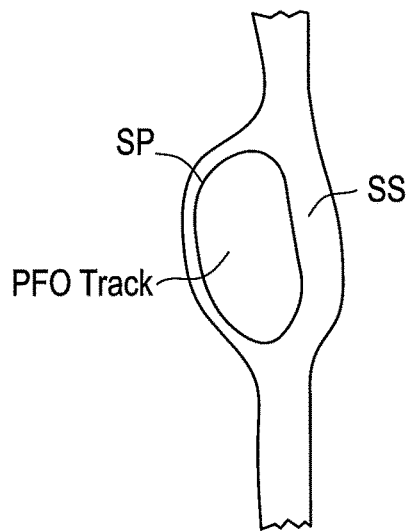
FIG. 4A is a cross-sectional view of the PFO track of FIG. 2 in an open configuration.
Figure 3:
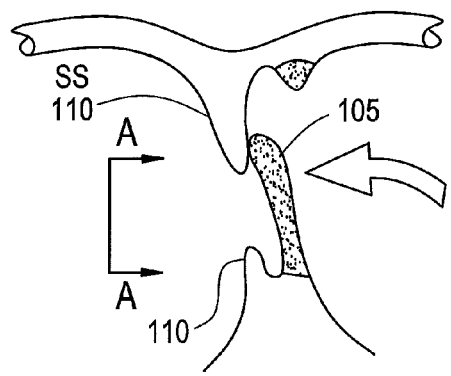
FIG. 3 is a close-up section view illustrating the PFO track held in the closed position by left atrial pressure.
Figure 4B:
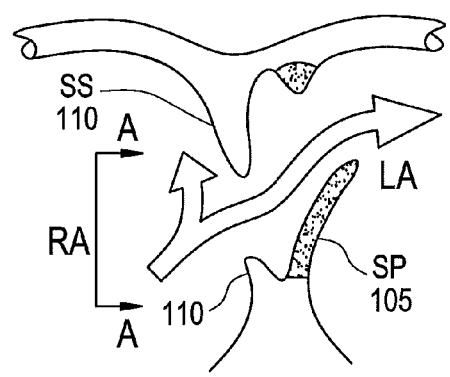
FIG. 4B is a close-up section view illustrating the PFO track in an open configuration.

The PFO results when either partial or no fusion of the septum primum 105 to the septum secundum 110 occurs. When this condition exists, a passageway (PFO track) 120 between the septum primum 105 and septum secundum 110 may allow communication of blood between the atria. This PFO track 120 is typically parallel to the plane of the septum primum 105, and has an opening that is generally oval in shape. FIG. 2 illustrates the opening of the PFO track 120 as viewed from an end of the track. Normally the opening is relatively tall, but quite narrow. The opening may be held closed by the mean pressure in the left atrium, which is typically higher than the right atrium. FIG. 3 is a close-up section view of the PFO track 120 held in the closed position by left atrial pressure. In this position, the septum primum 105 acts like a one-way valve, preventing fluid communication between the right and left atria through the PFO track 120. Occasionally, the pressure in the right atrium may temporarily be higher than the left atrium. When this condition occurs, the PFO track 120 opens and allow some fluid to pass from the right atrium to the left atrium, as indicated in FIGS. 4A and 4B. In particular, FIG. 4A is a cross-sectional view showing the PFO track of FIG. 2 in an open configuration. Similarly, FIG. 4B is a close-up section view illustrating the PFO track in an open configuration.

Although the PFO track 120 is often held closed, the endothelialized surfaces of the tissues forming the PFO track 120 prevent the tissue from healing together and permanently closing the PFO track 120. As can be seen in FIGS. 5A-5C, (a view from line "C-C" of FIG. 1), the septum primum 105 is firmly attached to the septum secundum 110 around most of the perimeter of the Fossa Ovalis 115, but has an opening along one side. The septum primum 105 is often connected, as shown, by two or more extensions of tissue along the sides of the PFO track 120 forming a tunnel.

Figure 5D:
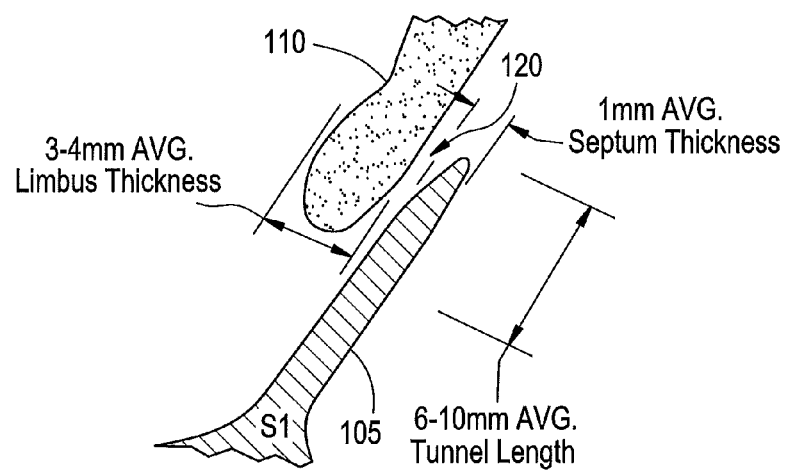
FIG. 5D is a close-up section view of the PFO track, showing the tunnel formed by the tissue extension.
Figure 5A:
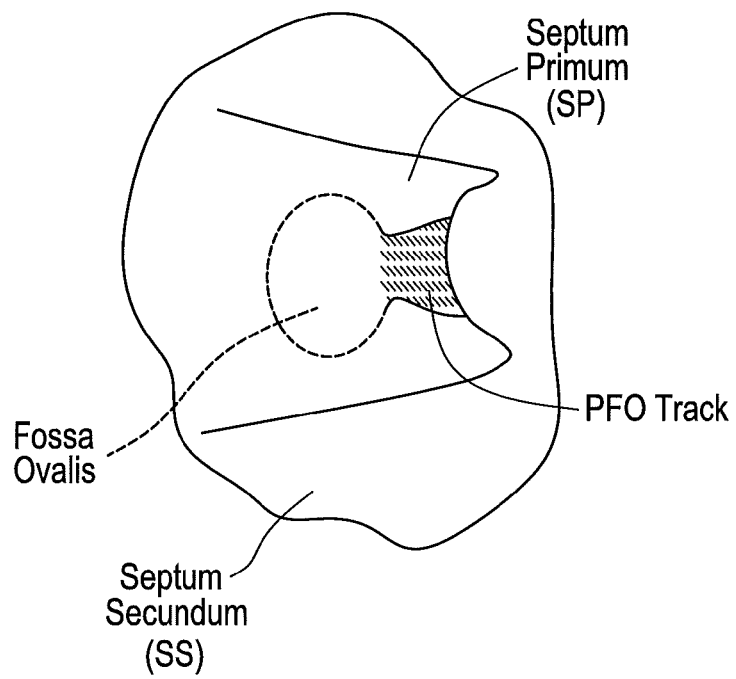
FIG. 5A is a cross-sectional view illustrating the PFO tract of FIG. 1.
Figure 5B:
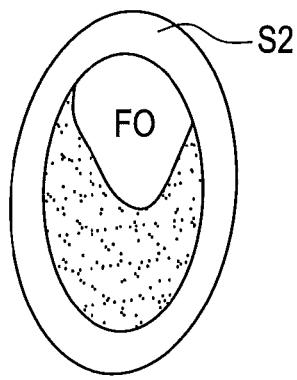
FIG. 5B is a section view taken along line A-A in FIG. 4B.
Figure 5C:
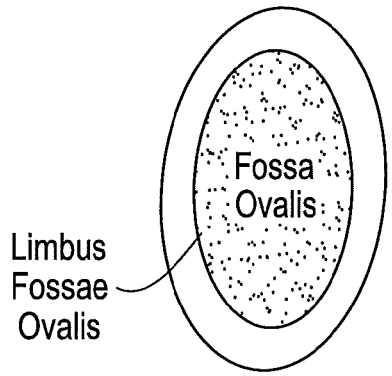
FIG. 5C is a section view taken along line A-A in FIG. 3.

FIG. 5D is a magnified section view of the PFO track 120, showing the tunnel formed by the tissue extensions. Typically, the tunnel length in an adult human can range between 2 and 13 mm.

The present invention relates to a system and method for closing a passageway in a body. In a particular embodiment, the device is used to close the Patent Foramen Ovale in a human heart. One of ordinary skill in the art would understand that similar embodiments could be used to close other passageways and openings in the body without departing from the general intent or teachings of the present invention.

Figure 6A:
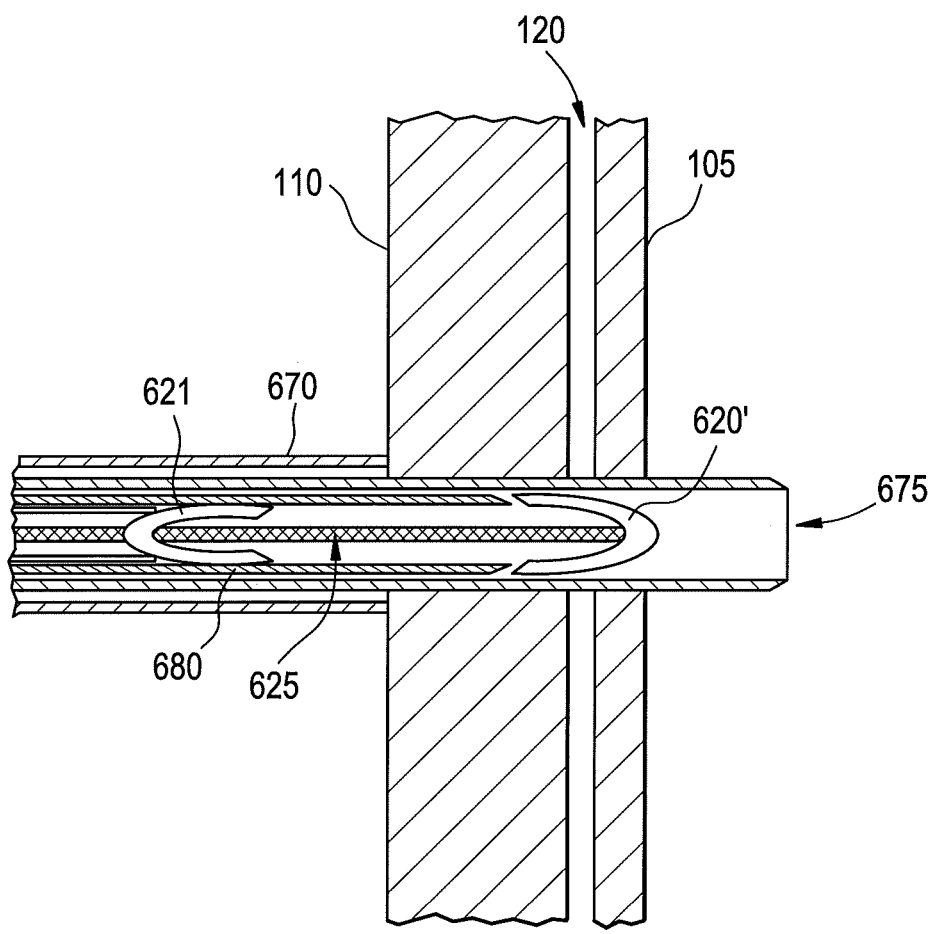
FIG. 6A is a perspective view illustrating the relationship between the components comprising the closure device and deployment device according to one aspect of the present invention.
Figure 6B:
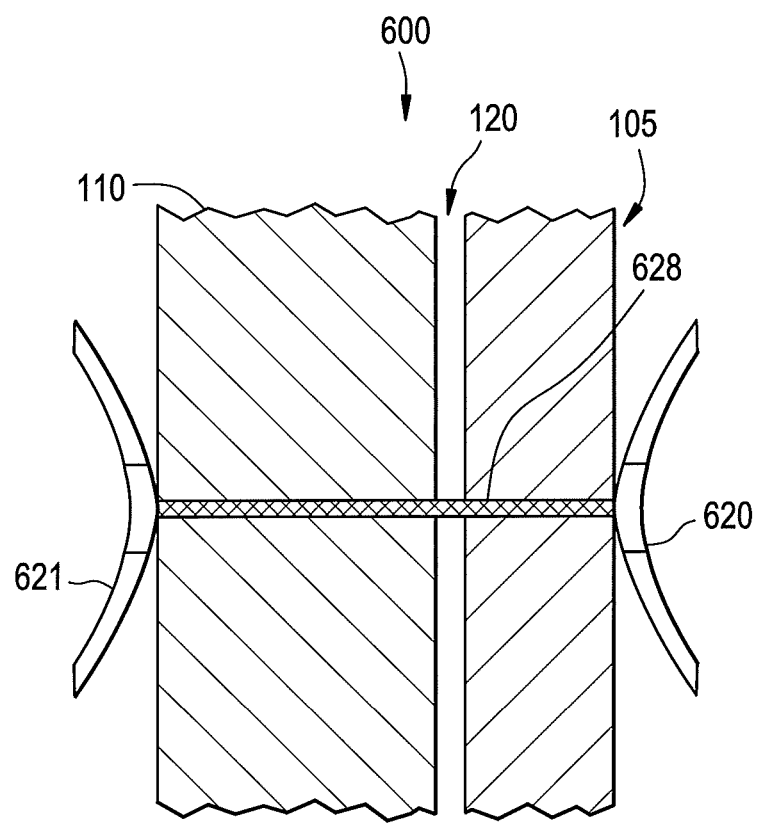
FIG. 6B illustrates the closure device deployed through the septum secundum and septum primum along the PFO track to close the PFO according to one embodiment of the present invention.

FIGS. 6A and 6B illustrate a device used to close the PFO according to one embodiment of the present invention. The device 600 comprises a flexible closure line 625 coupled to two expandable anchors 620, 621. Anchor 620 is coupled to distal end of the closure line 625, while anchor 621 is coupled to the proximal end of the flexible closure line 625. Anchor 621 is capable of sliding along closure line 625 and locking in desired location to cinch or take-up slack in closure line 625 length, bringing the proximal and distal anchors 621, 620 respectively, closer together and effectively bringing the septum secundum 110 and the septum primum 105 in close proximation.

It should be noted that the septum secundum 110 and the septum primum 105 do not have to be tightly touching to effect proper closure of the PFO. Instead, the septum secundum 110 and the septum primum 105 must just be brought close enough to minimize flow from atria to atria (typically flow from left atria to right atria).

The locking mechanism incorporated into anchor 621 may be a device capable of allowing the closure line 625 to slide through anchor 621 in one direction, and prevent sliding movement in the opposite direction. Examples of functionally similar commercial locking mechanisms include the DePuy Mitek RAPIDLOC™ device; zip ties; and similar linear locking devices known in the art.

Alternatively, the anchor 621 may be fixed to the closure line 625 at a predetermined distance from anchor 620. This may particularly be the case when the closure line 625 has an elastic or recoil ability and is capable of exerting tension when deployed, pulling the anchors 620, 621 together and effectively compressing the septum primum 105 to the septum secundum 110. In still a further embodiment of the invention, a closure device 600 may include an elastic closure line 625 and a slideable anchor 621. In this embodiment, the anchor 621 is capable of allowing the flexible closure line 625 to slide through the anchor 621 in one direction, and prevent sliding movement in the opposite direction, while the closure line 625 exerts tension between the two anchors 620, 621. These configurations should not necessarily be considered limiting, and other combinations of components are contemplated, such as, for example, both anchors 620 and 621 being slideable along a substantially elastic or inelastic closure line 625.

The closure line 625 may be any biocompatible filament known in the art that is capable of securing the septum primum 105 to the septum secundum 110. In a preferred embodiment the closure line 625 is a surgical suture, such as a multifilament non-biodegradable suture, or a forced entangled fiber filament. Alternatively, the closure line 625 may be made from an elastic material capable of exerting tension when stretched. In yet another alternative embodiment, the closure line 625 may be geometrically configured to exhibit structurally elastic behavior. In another alternative embodiment, the closure line 625 may be made from an anelastic material such as elastomeric polymers that are capable of exerting tension when stretched. In yet another alternative embodiment, the closure line 625 may be made from a super elastic material such as a nickel titanium alloy.

The anchors 620, 621 are expandable from a first, predeployed unexpanded configuration to a second expanded configuration. The anchors 620, 621 are preferably constructed from a structurally deformable material.

Structurally deformable materials are materials that can elastically or plastically deform without compromising their integrity. Geometric structures, such as anchors 620, 621, made from a deformable material are capable of changing shape when acted upon by an external force, or removal or an external force.

Geometric structures made from structurally deformable materials are typically self expanding or mechanically expandable. In a preferred embodiment, the anchors 620, 621 are made from a self-expanding material, such as Nitinol or a resilient polymer. However, the self-expanding anchors 620, 621 may also be made from an elastically compressed spring temper biocompatible metals. These self-expanding structures are held in a constrained configuration by an external force, typically a capture sheath, and elastically deform when the constraining force is released.

Some structurally deformable materials may also be mechanically expandable. Geometric structures can be mechanically expanded by introduction of an external force, through, for example, a mechanical expansion means. Mechanical expansion means are well known in the art and include balloon or cage expansion devices.

Once an external mechanical force is introduced to the geometric structure, the structure plastically deforms to its desired final configuration.

The anchors 620, 621 in their constrained state are capable of being held in a restrained low profile geometry for delivery, and assume an expanded shape capable of preventing the anchor 620, 621 from retracting through the septum primum 105 or septum secundum 110, as the case may be, once deployed.

Figure 7A:
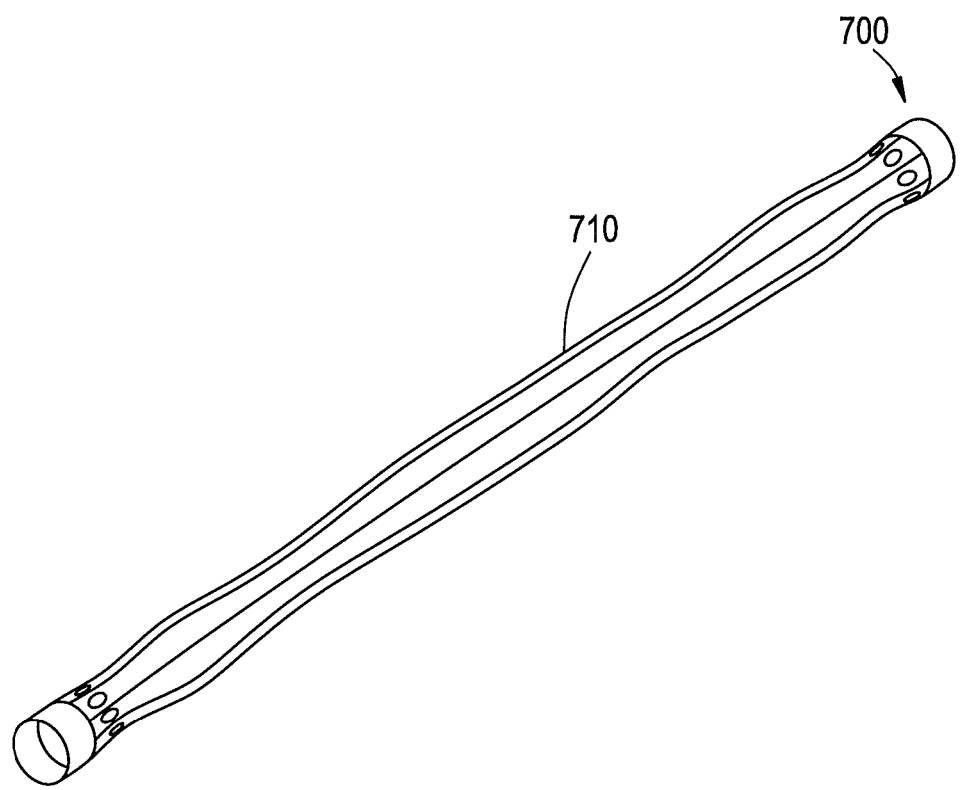
FIG. 7A is a perspective view of the anchor structure in the cut pre-expanded form according to one embodiment of the present invention.

In a preferred embodiment, the anchors 620, 621 are cut from a Nitinol hypotube 700 by methods known in the art. FIG. 7A is a perspective view of the anchor 620 in the cut pre-expanded form.

Figure 7B:
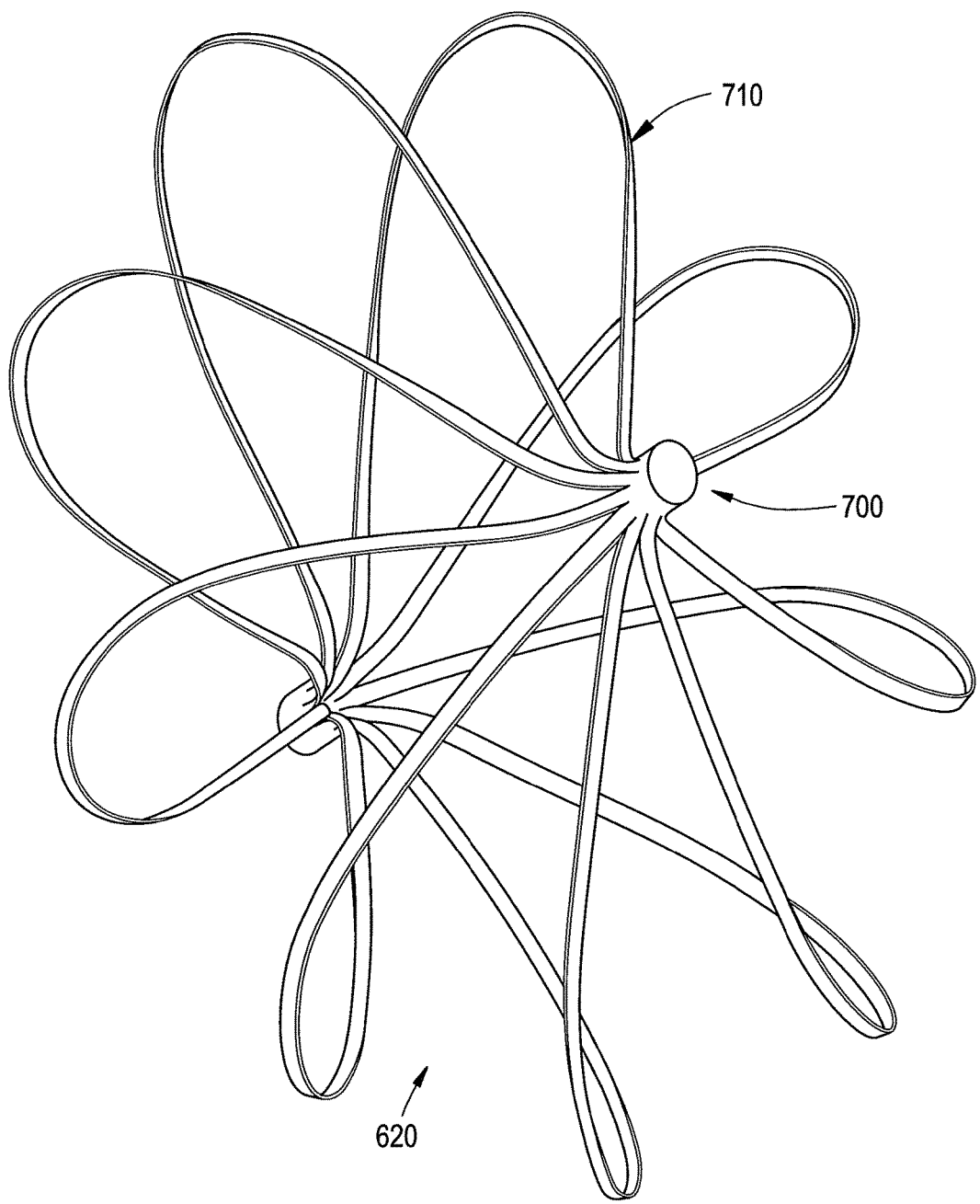
FIG. 7B is a perspective view of the expanded anchor according to one embodiment of the present invention.

The anchor 620 is then formed into a desired expanded configuration and annealed to assume a stress-free (relaxed) state. In one embodiment of the invention, the anchor 620, 621 is formed into a basket shaped configuration, having a plurality of legs 710. A perspective view of the expanded basket anchor 620 according to one embodiment of the present invention is illustrated in FIG. 7B.

Figure 7C:
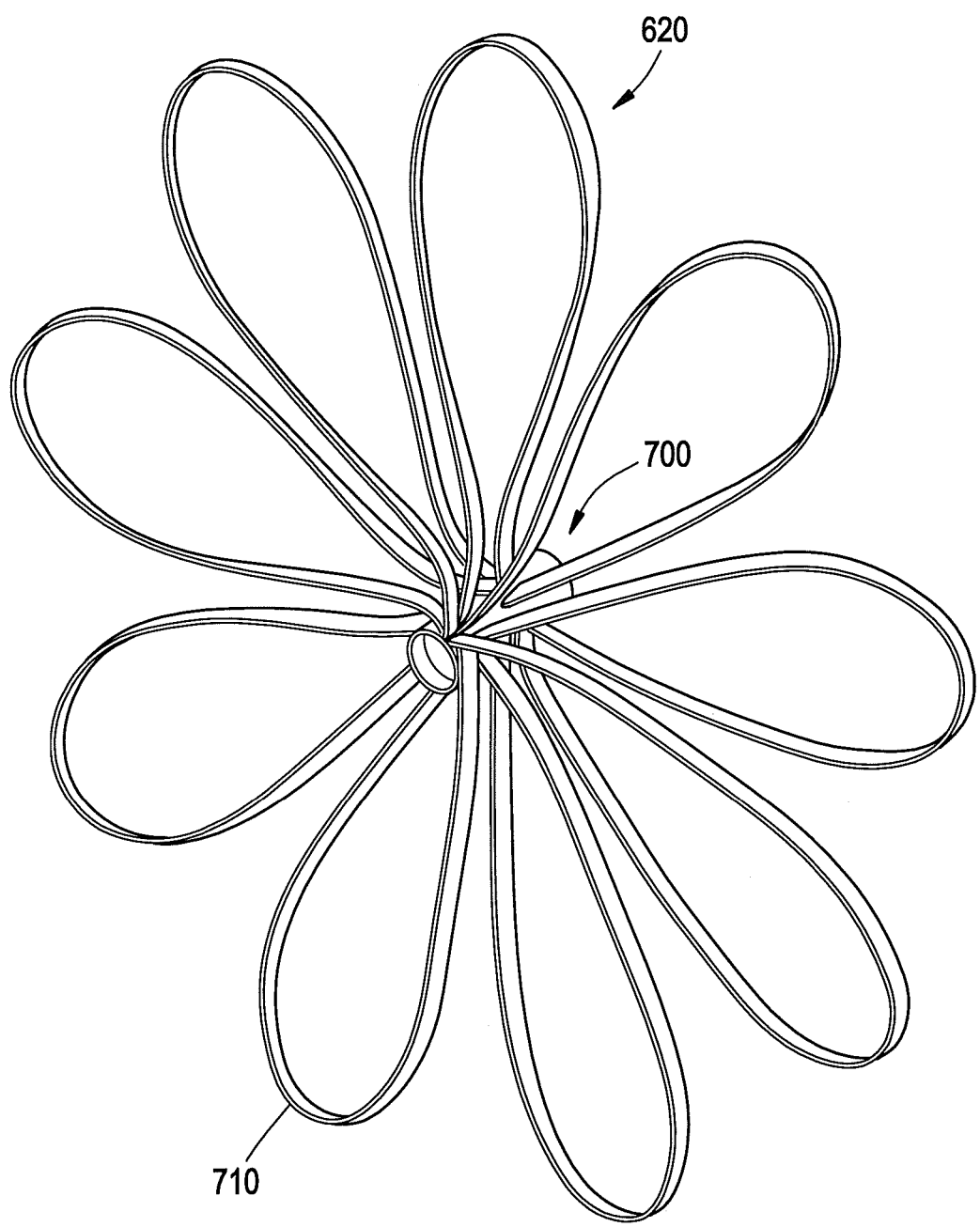
FIG. 7C is a perspective view of the anchor under tensioning of the closure line according to one embodiment of the present invention.

Once the closure device 600 is deployed, the basket shaped anchors 620, 621 collapse under tensioning of the closure line 625, into a flattened "flower petal" shape as illustrated in FIG. 7C. In this state, the anchors 620, 621 are under strain. The super elastic properties of the anchors 620, 621 under strain exert an axially outward force against the adjacent tissue, putting the closure line 625 in tension.

Figure 8A:
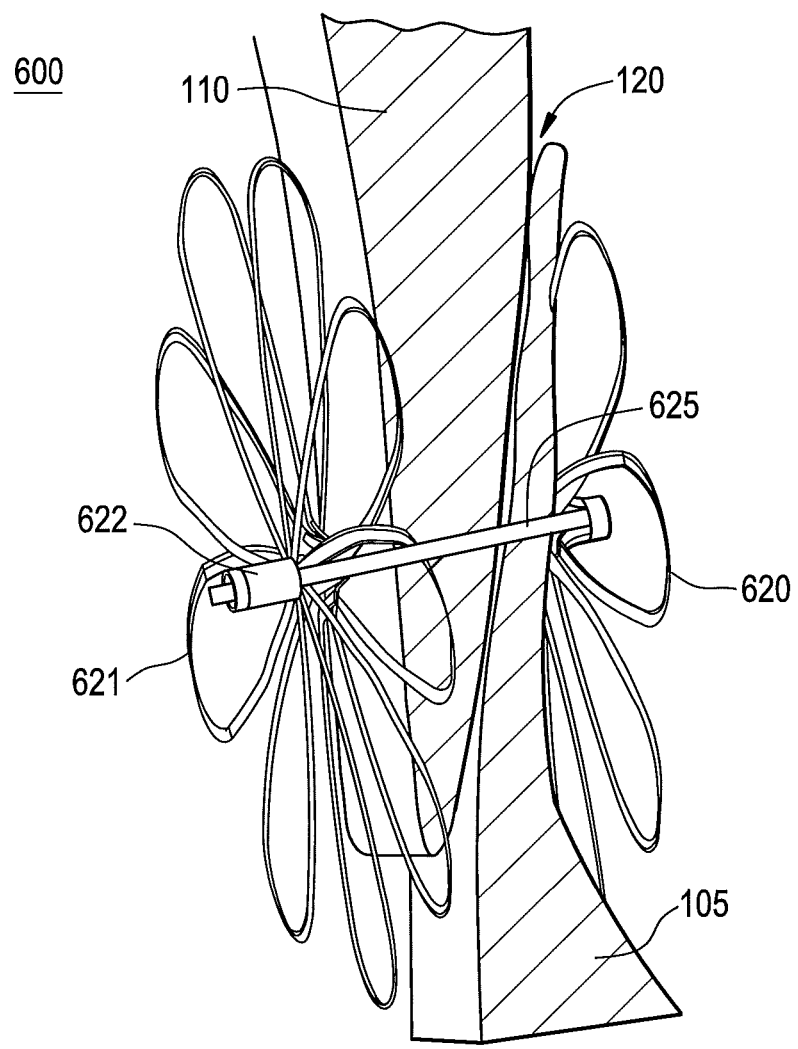
FIG. 8A illustrates substantial closure of the PFO track with the closure device deployed through the septum secundum and septum primum along the PFO track to close the PFO according to one embodiment of the present invention.

FIG. 8A illustrates the closure device 600 having flower petal shaped anchors 620, 621 deployed through the septum secundum and septum primum along the PFO tract to close the PFO according to one embodiment of the present invention. The proximal anchor 621 in FIG. 8A also includes a locking mechanism 622 integrated therein.

This anchor design should not be considered a limiting feature of the invention, as other shapes and configurations of anchors 620, 621 are also contemplated by the present design. This may include, for example, expandable disc design, star design, j-hook design, or any expandable geometric shape. In addition other materials exhibiting similar characteristics, such as non-biodegradable swellable polymers, are similarly contemplated by the present invention. Still, other designs for anchors 620, 621 may include long-aspect dimensioned objects axially aligned in needles 605, 610 in the constrained state. Once deployed, the long axis of the anchor 620, 621 rotates substantially perpendicular to the needle 605, 610 longitudinal axis, effectively anchoring the closure line 625 in place.

Although FIG. 8A illustrates the closure device 600 deployed through the septum secundum 110 and septum primum 105 along the PFO track 120, it should be understood that the closure device 600 may be deployed through other locations to achieve the same results. In addition, each of the FIGS. 8A through 8F illustrate the anchors 620, 621 and closure line 625 in a particular orientation. It should be understood that position of the anchor structures 620, 621 may be reversed.

FIGS. 8B through 8F illustrate the closure device 600 deployed at various locations across the septum primum 105 and/or septum secundum 110. Although the penetration through the septum primum 105 and/or septum secundum 110 are shown at different locations, common to each of the illustrated deployments is the location of the distal anchor 620 and the proximal anchor 621 in the left and right atrial chambers respectively.

Figure 8B:
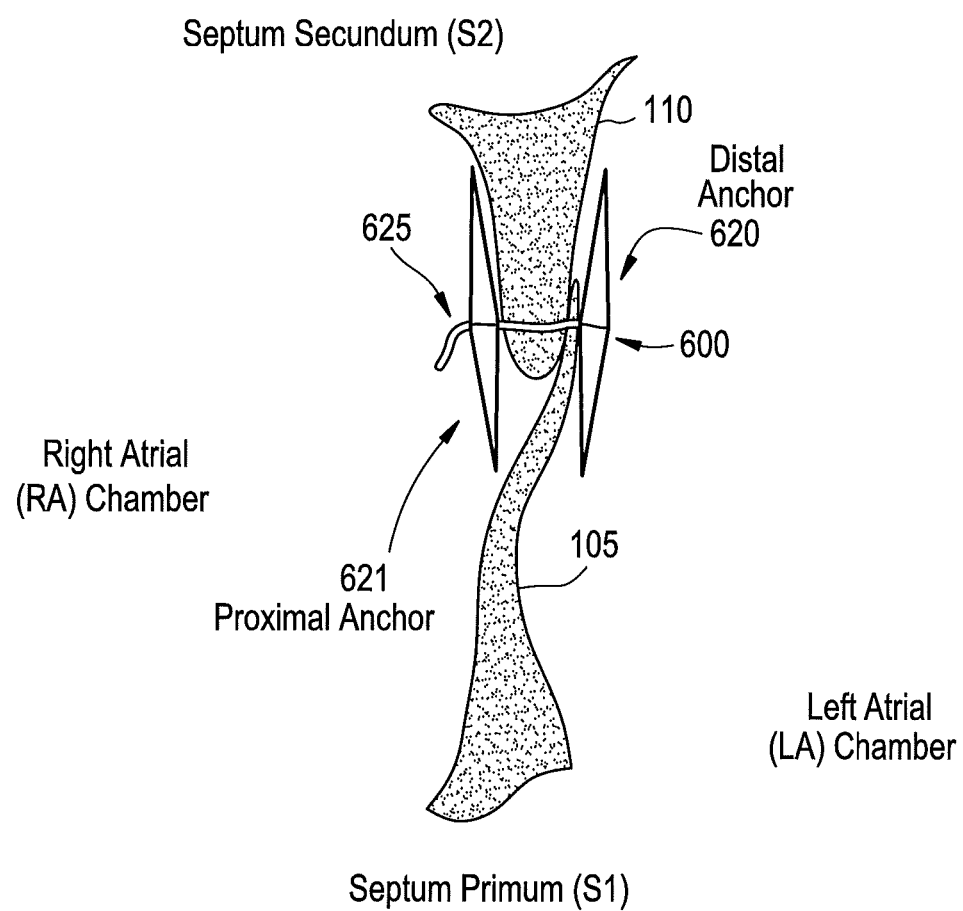
FIG. 8B illustrates substantial closure of the PFO tract with a single penetration through both the septum primum and septum secundum according to one embodiment of the present invention.

FIG. 8B illustrates substantial closure of the PFO tract 120 with a single penetration through both the septum primum 105 and septum secundum 110.

It should be noted that both the septum primum 105 and septum secundum 110 do not have to be penetrated to maintain close enough proximity between the septal tissues to achieve proper closure of the PFO. FIG. 8C illustrates substantial closure of the PFO with a single penetration only through the septum primum 105. In the illustrated embodiment, there is significant overlap between the septum primum 105 and septum secundum 110 creating a fairly long track 120. The distal and proximal anchors 620, 621 respectively are sized to exert enough force on the septum primum 105 and septum secundum 110 to facilitate closing of the PFO track 120 when the closure line 625 is tensioned.

Figure 8D:
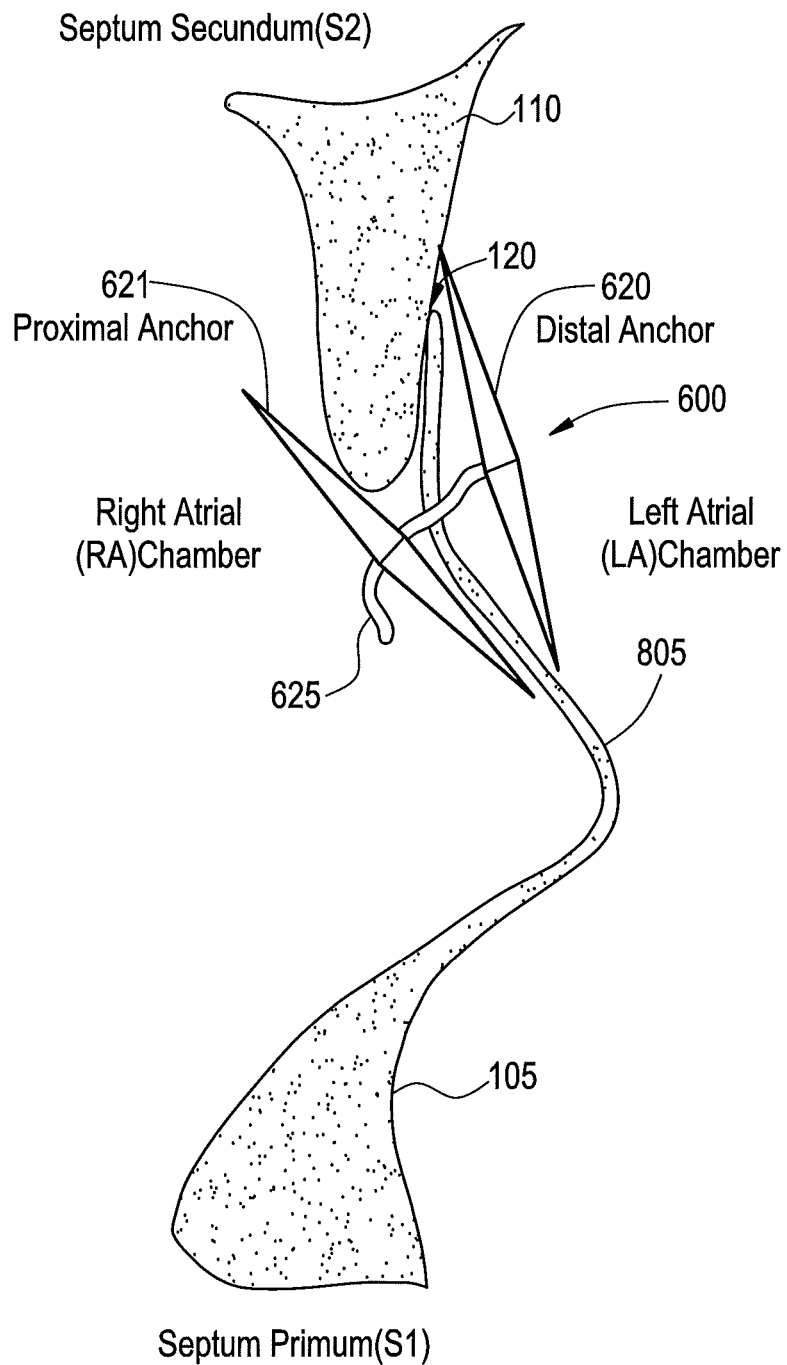
FIG. 8D illustrates substantial closure of the PFO, where an ASA is present, with a single penetration only through the septum primum according to one embodiment of the present invention.

The PFO closure device 600 can be used to facilitate closing the PFO track 120 when other defects in the septal wall are present. For example, the PFO closure device 600 may be used when an atrial septal aneurysm (ASA) 805 is present. An ASA is characterized as a saccular deformity, generally at the level of the fossa ovale, which protrudes to the right or left atrium, or both. FIG. 8D illustrates substantial closure of the PFO, where an ASA is present, with a single penetration only through the septum primum 105. However, the distal and proximal anchors, 620 and 621 respectively, are sized to contact both the septum primum 105 and septum secundum 110 to facilitate closing of the PFO track 120.

Figure 8E:
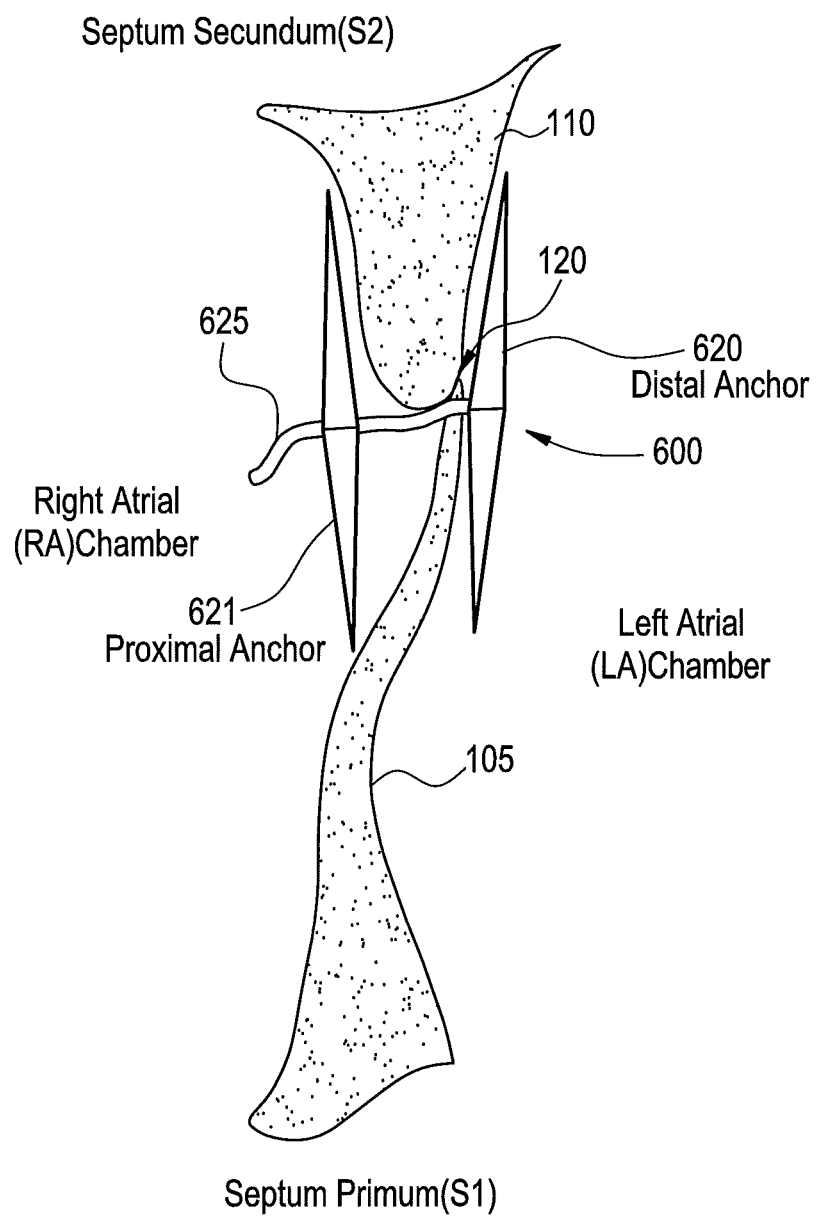
FIG. 8E illustrates substantial closure of the PFO with a single penetration through the septum primum according to one embodiment of the present invention.

The single penetration method may also be employed where there is minimal overlap between the septum primum 105 and septum secundum 110. This so called "short tunnel" PFO may not be readily closed with prior art "intra-tunnel methods. FIG. 8E illustrates substantial closure of the PFO with a single penetration through the septum primum 105.

Figure 8F:
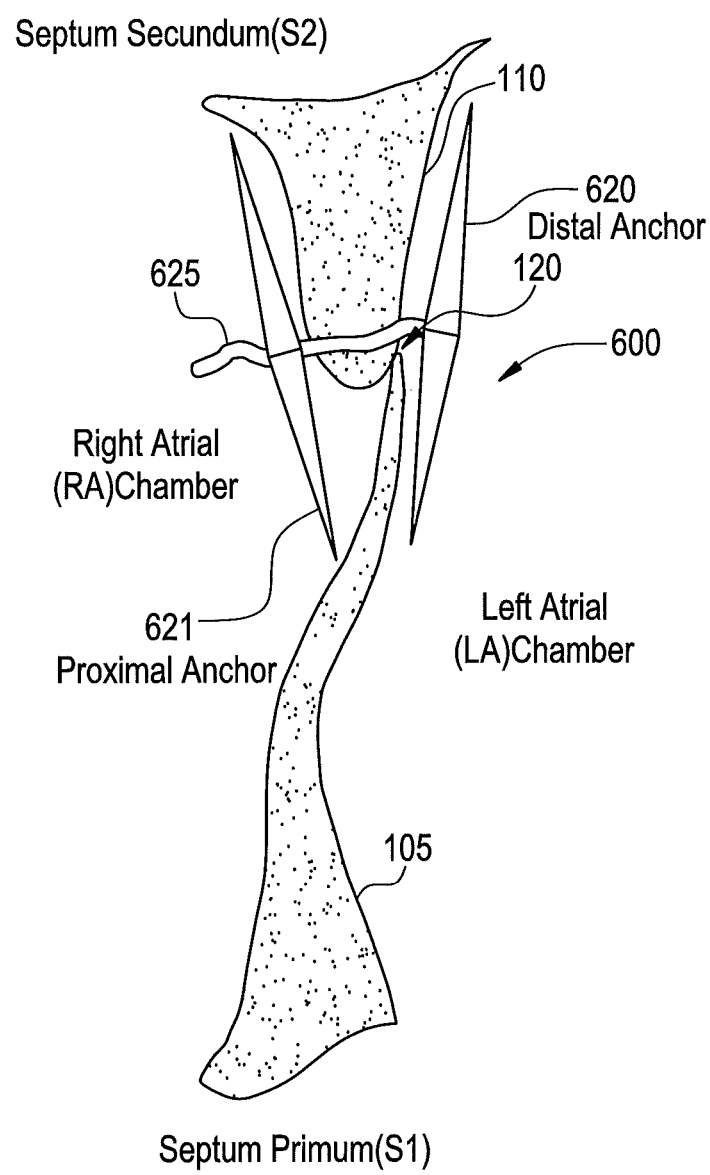
FIG. 8F illustrates the deployment of the closure device through a single penetration in the septum secundum according to one embodiment of the present invention.

Similar to the single penetration method illustrated in FIGS. 8A through 8E, the closure device 600 may be deployed using a single penetration through the septum secundum 110 as illustrated in FIG. 8F.

The present invention utilizes a removable deployment device to introduce the mechanical closure device 600 into the atrium of the heart, preferably through a minimally invasive, transluminal procedure.

Minimally invasive heart surgery refers to several approaches for performing heart operations that are less difficult and risky than conventional open-heart surgery. These approaches restore healthy blood flow to the heart without having to stop the heart and put the patient on a heart-lung machine during surgery. Minimally invasive procedures are carried out by entering the body through the skin, a body cavity or anatomical opening, but with the smallest damage possible to these structures. This results in less operative trauma for the patient. It also less expensive, reduces hospitalization time, causes less pain and scarring, and reduces the incidence of complications related to the surgical trauma, speeding the recovery.

One example of a minimally invasive procedure for performing heart surgery is a trans-thoracic laparoscopic (endoscopic) procedure. The part of the mammalian body that is situated between the neck and the abdomen and supported by the ribs, costal cartilages, and sternum is known as the thorax. This division of the body cavity lies above the diaphragm, is bounded peripherally by the wall of the chest, and contains the heart and lungs. Once into the thorax, the surgeon can gain access to the atrium of the heart through an atriotomy, a surgical incision of an atrium of the heart. For example, if the surgeon wishes to gain access to the right atrium they will perform an atriotomy in the right atrial appendage.

The primary advantage of a trans-thoracic laparosopic procedure is that there is no need to make a large incision. Instead, the surgeon operates through 3 or 4 tiny openings about the size of buttonholes, while viewing the patient's internal organs on a monitor. There is no large incision to heal, so patients have less pain and recover sooner. Rather than a 6- to 9-inch incision, the laparoscopic technique utilized only 4 tiny openings—all less than ½ inch in diameter.

Another minimally invasive technique for gaining access to the heart and deploying the closure device is a percutaneous transluminal procedure. Percutaneous surgical techniques pertain to any medical procedure where access to inner organs or other tissue is done via needle-puncture of the skin, rather than by using an "open" approach where inner organs or tissue are exposed (typically with the use of scalpel). The percutaneous approach is commonly used in vascular procedures, where access to heart is gained through the venous or arterial systems. This involves a needle catheter getting access to a blood vessel, followed by the introduction of a wire through the lumen of the needle. It is over this wire that other catheters can be placed into the blood vessel. This technique is known as the modified Seldinger technique. The PFO closure device 600 may also be deployed via percutaneous methods by steerable catheters or guidewires.

In the Seldinger technique a peripheral vein (such as a femoral vein) is punctured with a needle, the puncture wound is dilated with a dilator to a size sufficient to accommodate an introducer sheath, and an introducer sheath with at least one hemostatic valve is seated within the dilated puncture wound while maintaining relative hemostasis.

Penetration of the interatrial septum requires piecing the septal wall. In a preferred embodiment this penetration is accomplished by using a needle, trocar or similar device to accomplish non-core cutting of the interatrial septum. In one embodiment of the invention, the non-core cutting device is a tubular needle-like structure, however other configurations and shaped structures may be used as would be understood by one skilled in the art. The needle tube is a substantially rigid structure capable of penetrating the septum secundum 110 and septum primum 105 along the PFO track 120. The needle is preferably sized to be 13 French or smaller, most preferably 10 French or smaller, and made from a biocompatible material, such as, for example surgical stainless steel, Nitinol, or Cobalt-Chromium alloys. It should be understood that these materials are not meant to limit the scope of the invention. Any biocompatible material capable of being sharpened and holding a sharp edge, and having sufficient strength to facilitate penetration through the septum secundum 110 and/or septum primum 105, may be suitable. The needle is constructed with a tapered distal end, as is known in the art. In a preferred embodiment, the geometric configuration of the tapered distal end is optimized to minimize induced tissue trauma at the site of penetration. In addition, the needle is of sufficient body length to penetrate both the septum secundum 110 and septum primum 105, while still maintaining the needed size and axial flexibility to navigate the tortuous vessel anatomy when being delivered to the heart percutaneously.

In another embodiment of the invention, penetrating the interatrial septum may be accomplished by drilling through the septum.

With the introducer sheath in place, the guiding catheter or delivery member 630 of the closure device is introduced through the hemostatic valve of the introducer sheath and is advanced along the peripheral vein, into the region of the vena cavae, and into the right atrium.

In one embodiment of the invention, the distal tip of the delivery device 630 is positioned against the interatrial septal wall. In the case of a septum having a PFO, the interatrial septal wall may be the septum primum 105 and/or septum secundum 110, as the case may be. A needle or trocar associated with the delivery device 630 is then advanced distally until it punctures the septum primum 105 and or septum secundum 110. A separate dilator may also be advanced with the needle through the septum primum 105 and/or septum secundum 110 to prepare an access port through the septum primum 105 and/or septum secundum 110 for seating the delivery device 630. The delivery device 630 traverses across the septum and is seated in the left atrium, thereby providing access for closure devices 600 through its own inner lumen and into the left atrium.

It is however further contemplated that other left atrial access methods may be suitable substitutes for using the delivery device 630 and closure device 600 of the present invention. In one alternative variation not shown, a "retrograde" approach may be used, wherein the delivery device 630 is advanced into the left atrium from the arterial system. In this variation, the Seldinger technique is employed to gain vascular access into the arterial system, rather than the venous, for example, at a femoral artery. The delivery device 630 is advanced retrogradedly through the aorta, around the aortic arch, into the ventricle, and then into the left atrium through the mitral valve.

Once in the desired atrium of the heart the closure device 600 is deployed transeptally from one atria to the other. For the purpose of this invention, transeptally is defined as deployment from one atria to the other through the septum (septum primum 105 and/or septum secundum 110), as opposed to intra-atrial access through the PFO tract 120 (tunnel). In the case of a heart having a patent foramen ovale, transeptal penetration may be through the septum primum (SP) 105 and/or septum secundum (SS) 110, or visa versa, whichever the case may be. Preferably, the angle of transeptal penetration is between 45 and 135 degrees to the surface of the septum, but is most preferably orthogonal to the surface of the septum.

By way of example, in one embodiment of the present invention using right atrial access, the right atrium is first accessed by the delivery device 630 (and closure device 600). The closure device 600 may then be deployed by penetrating the interatrial septum (septum primum 105 and/or septum secundum 110) from the right atrial chamber to the left atrial chamber in the heart, and deploying the distal anchor 620 associated with the closure device 600 into the left atrial chamber. After successful deployment of the distal anchor 620, the delivery device 630 may be partially withdrawn from the left atrial chamber to the right atrial chamber, leaving the distal anchor 620 in place. The proximal anchor 621 associated with the closure device 600 can then be deployed into the right atrial chamber. This substantially linear atrial deployment method is shown in FIGS. 8A through 8F.

Similar procedures are employed when left an atrial access technique is used. For example, in one embodiment of the present invention using left atrial access, the left atrium is first accessed by the delivery device 630 (and closure device 600). The closure device 600 may then be deployed by penetrating the interatrial septum (septum primum 105 and/or septum secundum 110) from the left atrial chamber to the right atrial chamber in the heart, and deploying the distal anchor 620 associated with the closure device into the first atrium. After successful deployment of the distal anchor 620, the delivery device 630 may be partially withdrawn from the right atrial chamber to the left atrial chamber, leaving the distal anchor 620 in place. The proximal anchor 621 associated with the closure device can then be deployed into the left atrial chamber.

Once the proximal anchor is deployed, the closure device may be cinched to bring the proximal and distal anchors closer together. This results in the septum secundum 110 and the septum primum 105 being brought in close proximation to facilitate closure of the Patent Foramen Ovale. It should be noted that the septum secundum 110 and the septum primum 105 do not have to be tightly touching to effect proper closure of the PFO. Instead, the septum secundum 110 and the septum primum 105 must just be brought close enough to minimize flow from atria to atria (typically flow from right atria to left atria).

To achieve and maintain the proximity between the septum secundum 110 and the septum primum 105, it may be necessary to adjust the proximal anchor by uni-axially cinching or sliding the proximal anchor 620 along closure line 625. In one embodiment of the invention, cinching comprises uni-axially adjusting the proximal anchor relative to a closure line associated with the closure device. In another embodiment of the invention, cinching comprises incrementally adjusting the proximal anchor relative to a closure line associated with the closure device.

Once the closure device is cinched in place the method may further comprise assessing the degree of proximation between the septum secundum 110 and the septum primum 105.

In one embodiment of the invention, the clinician may visually assess the proximation though an endoscopic or fluoroscopic procedure. In addition, other methods may be used to measure the proximation between the septum secundum 110 and the septum primum 105, such as through pressure observation or infrared imaging.

After proper cinching, any unwanted length of closure line 625 that remains unconstrained within the right atrium may be mechanically removed. Devices known in the art capable of removing the excess closure line 625 include catheter-based snare and cut devices. In addition to independent devices, a mechanical cut and removal mechanism may be integrated into the deployment device.

The closure device will then be in position, with the anchors 620, 621 opened against the septum secundum 110, and the closure line 625 connecting the anchors 620, 621 through the septum primum 105 and septum secundum 110, thus holding the septum primum 105 in place.

Another embodiment of the invention may include a location monitoring system to facilitate placement of the deployment device 630. In particular, the location monitoring device will assist in determining whether the clinician is in the correct chamber of the heart.

Figure 10:
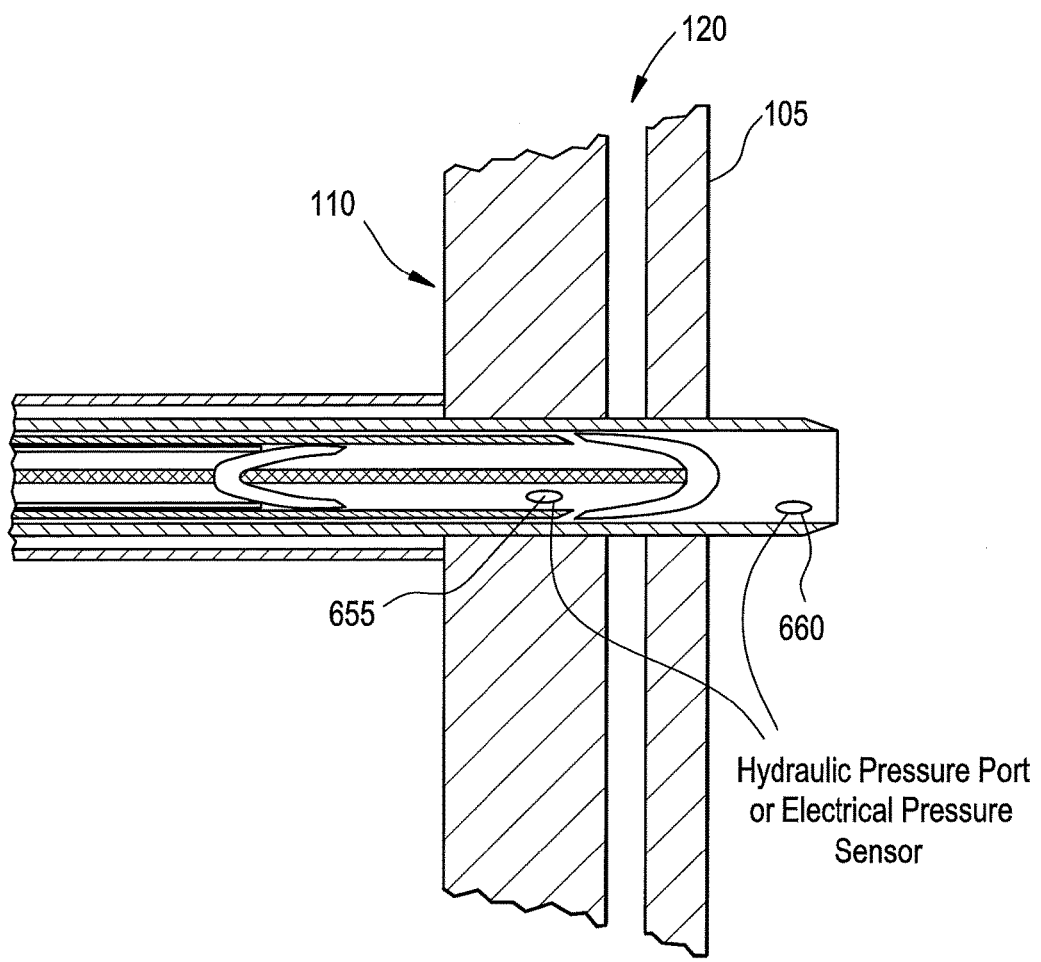
FIG. 10 is a perspective view illustrating exemplary sensors, such as a hydraulic pressure port sensor and electrical pressure transducer.

In a preferred embodiment, the location monitoring system includes the ability to measure localized pressure relative to the distal end of the deployment device 630. The pressure measurement read by the location monitoring system may be achieved by electronic, mechanical and/or physical means, such as a solid-state pressure transducer, spring loaded diaphragm, hydraulic pressure port, and/or communicating manometer. These and other pressure measurement techniques would be known by one of skill in the art. FIG. 10 is a perspective view illustrating exemplary sensors, such as a hydraulic pressure port 655 or electrical pressure transducer 660.

By way of example it is well known that pressures vary in different locations within the cardiovascular system. Specifically, gage pressure in the right and left atrium are know to range from approximately 1-6 mmHg to 10 mmHg respectfully. Similarly, gage pressure within the ascending aorta ranges from approximately 120 to 160 mmHg during systole.

Before deployment, the clinician will first monitor pressure within the right atrium. This reading should indicate a pressure of 1-6 mmHg. The distal end of the outer needle 605 will be inserted through the septal wall (septum primum 105 and/or septum secundum 110) and into the left atrium. The monitored pressure should change to approximately 10 mmHg. A much higher reading, such as in the range of approximately 120 to 160 mmHg, indicates puncture of the aorta. The clinician will then have to retract the outer needle 605 and reposition the delivery device 630 for re-entry. Similarly, once in the left atrium the inner needle 610 is advanced back into the right atrium. The clinician should observe a pressure change from 10 mmHg to 1-6 mmHg.

For delivery to the heart, the deployment device 630 (and thus the closure device 600) is used in conjunction with an accessory device (not shown) known in the art. In a preferred embodiment, the accessory device may be a guiding catheter that tracks over a guidewire, and is steered through the vasculature into the right atrium.

In another embodiment, the accessory device and deployment device 630 may be formed as an integrated component, capable of being steered through the vasculature.

Figure 9A:
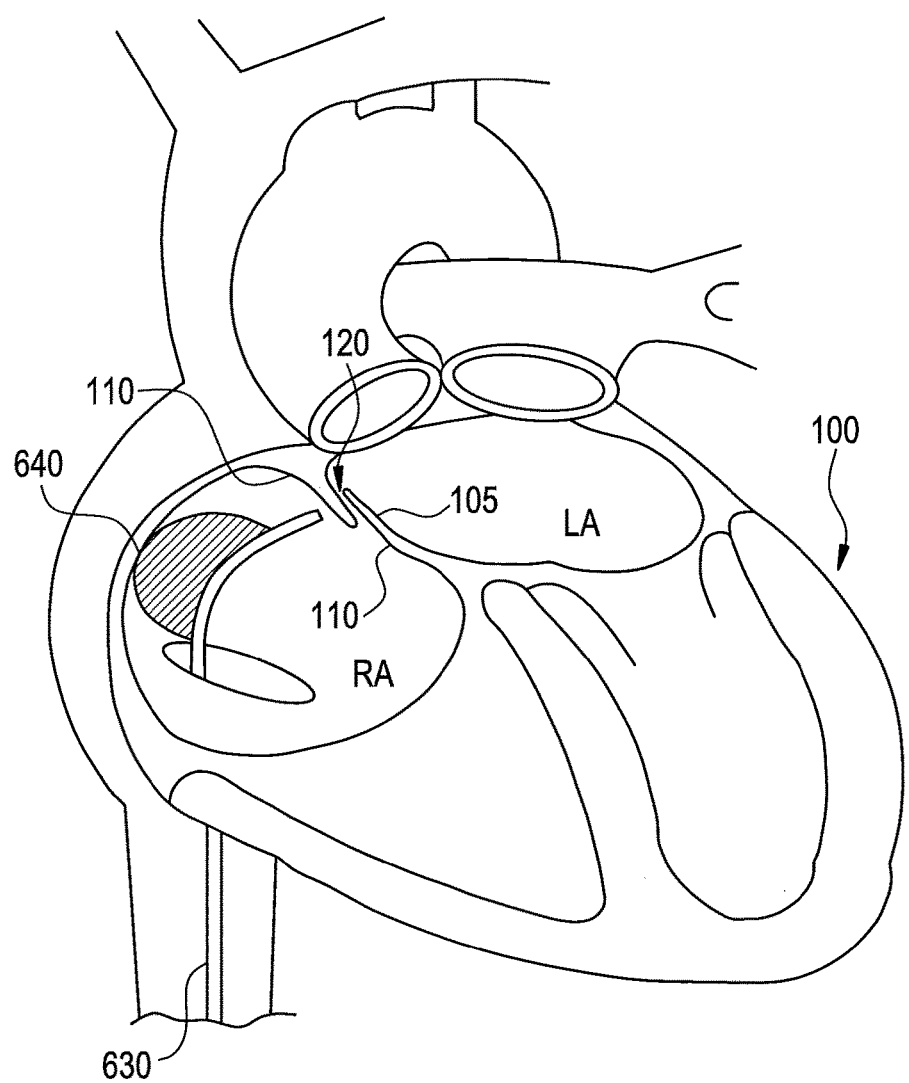
FIG. 9A is a section view of the heart illustrating a deployment device having backup support in the form of an axially asymmetric spline according to one embodiment of the present invention.
Figure 9B:
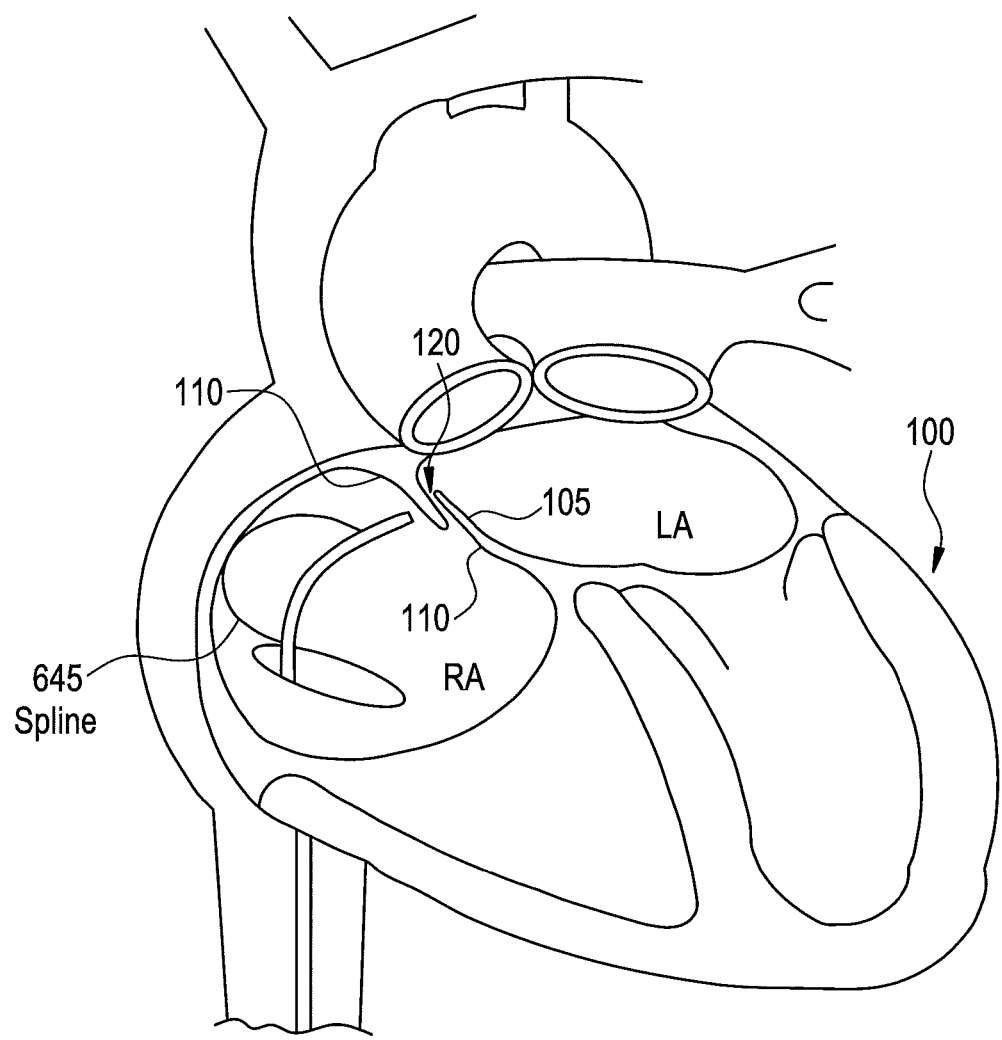
FIG. 9B is a section view of the heart illustrating a deployment device having backup support in the form of an axially asymmetric balloon according to one embodiment of the present invention.
Figure 9C:
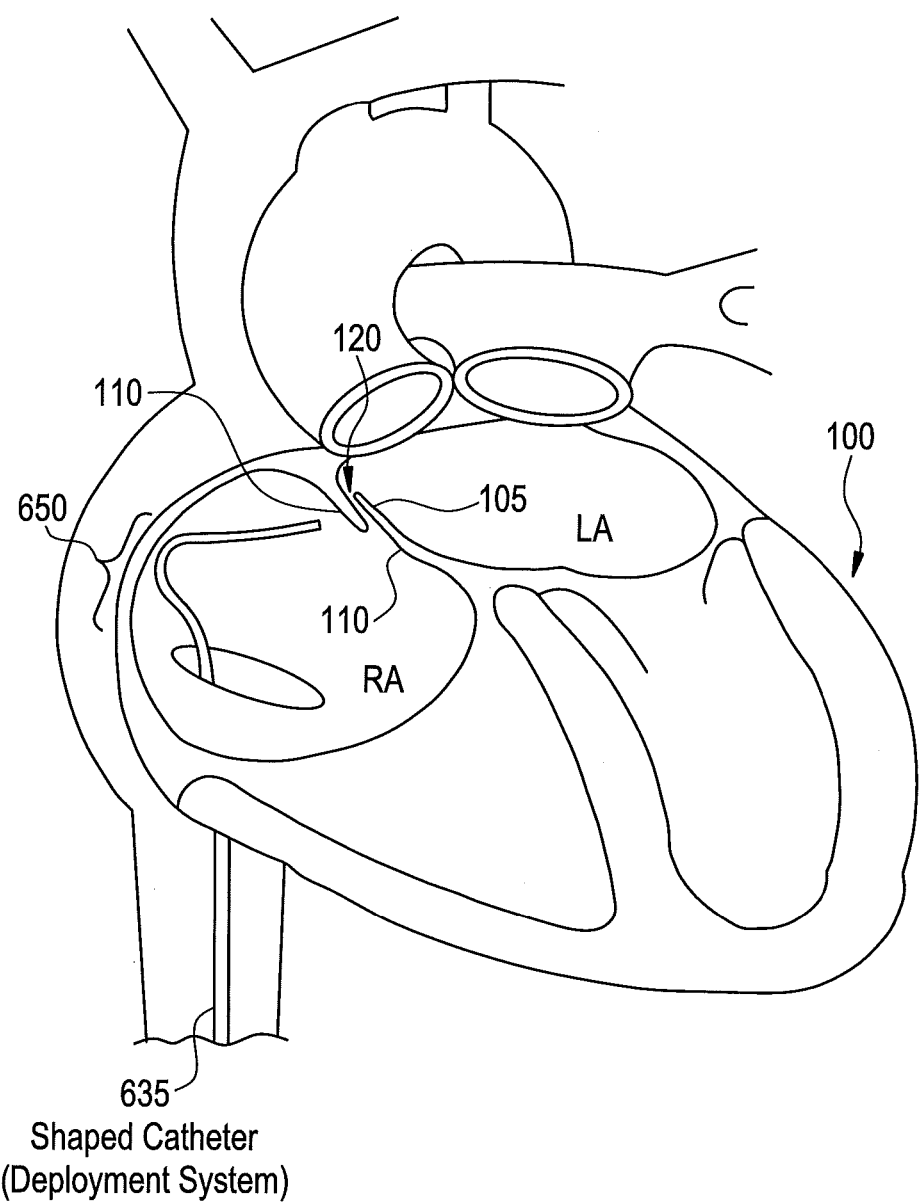
FIG. 9C is a section view of the heart illustrating a deployment device with a shape along the distal end to provide backup support, according to one embodiment of the present invention.

To facilitate deployment of the closure device 600, the deployment device 630 may include features that provide backup support. This backup support may include, for example: an axially asymmetric expansion member attached along an outer shaft 635, such as a balloon or self expanding cage 640; a spline 645; or imparting a shape 650 along the body of the deployment device 630. Examples of these backup support features are illustrated in FIGS. 9A through 9C, respectively. It should be understood that the outer shaft 635 may be part of the guiding catheter, or integrated into the deployment device 630. These and other such backup support devices would be understood by one of skill in the art. These backup support features can also be incorporated onto accessory devices, such as the guide catheter.

Still other embodiments utilizing known methods and apparatus to deliver the deployment device 630 and closure device 600 into the atrium of heart 100 would be obvious to one of skill in the art.

In one embodiment of the invention, the deployment device 630 is part of a guiding catheter assembly, including a delivery catheter 670 coaxially oriented and slideably engaged over a distal catheter 675, which may be coaxially oriented and slideably engaged over a proximal catheter 680. A needle assembly 605 is similarly coaxially oriented and slideably engaged within the distal catheter 675.

The distal tip of a guiding catheter is first positioned within the right atrium according to a transeptal access method, which is further described in more detail as follows. The right venous system is first accessed using the "Seldinger" technique, wherein a peripheral vein (such as a femoral vein) is punctured with a needle, the puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or sheath is introduced through the hemostatic valve of the introducer sheath and is advanced along the peripheral vein, into the region of the vena cavae, and into the right atrium.

Figure 11:
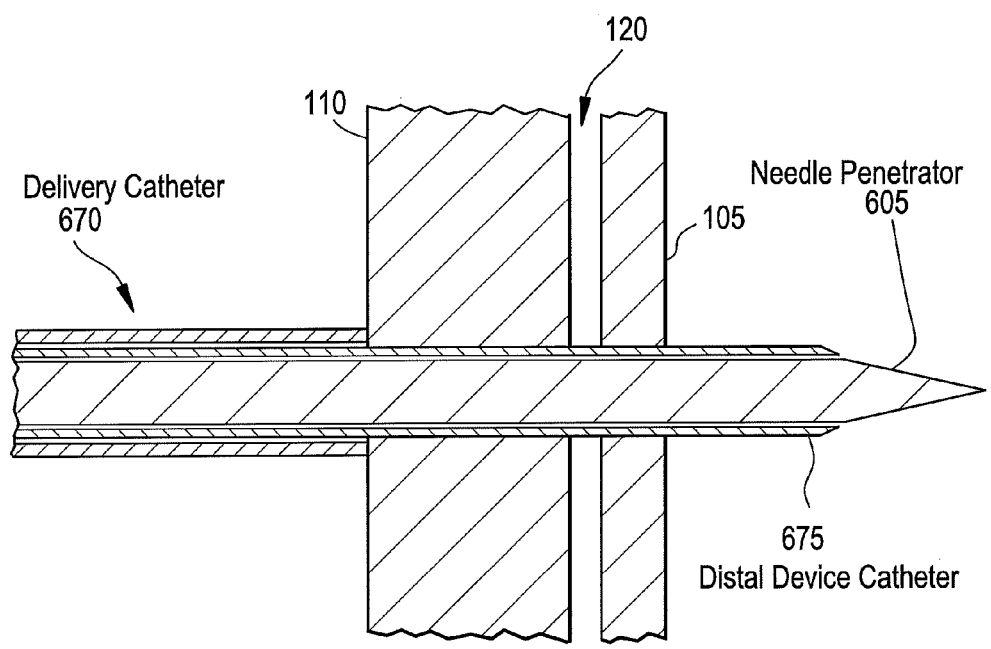
FIG. 11 is a perspective view showing the relationship between components comprising the deployment device and closure device after the needle punctures through the septum secundum and septum primum into the left atrium, according to one embodiment of the present invention.

Once in the right atrium, the distal tip of the guiding catheter is positioned against the septum secundum 110 in the intra-atrial septal wall. The needle 605 is then advanced distally through the distal device catheter 675 until the needle 605, and distal device catheter 675 puncture through both the septum secundum 110 and septum primum 105 into the left atrium. The configuration of the deployment device 630, including the needle 605 and distal device catheter 675, puncturing through the septum secundum 110 and septum primum 105 is shown in FIG. 11.

Figure 12:
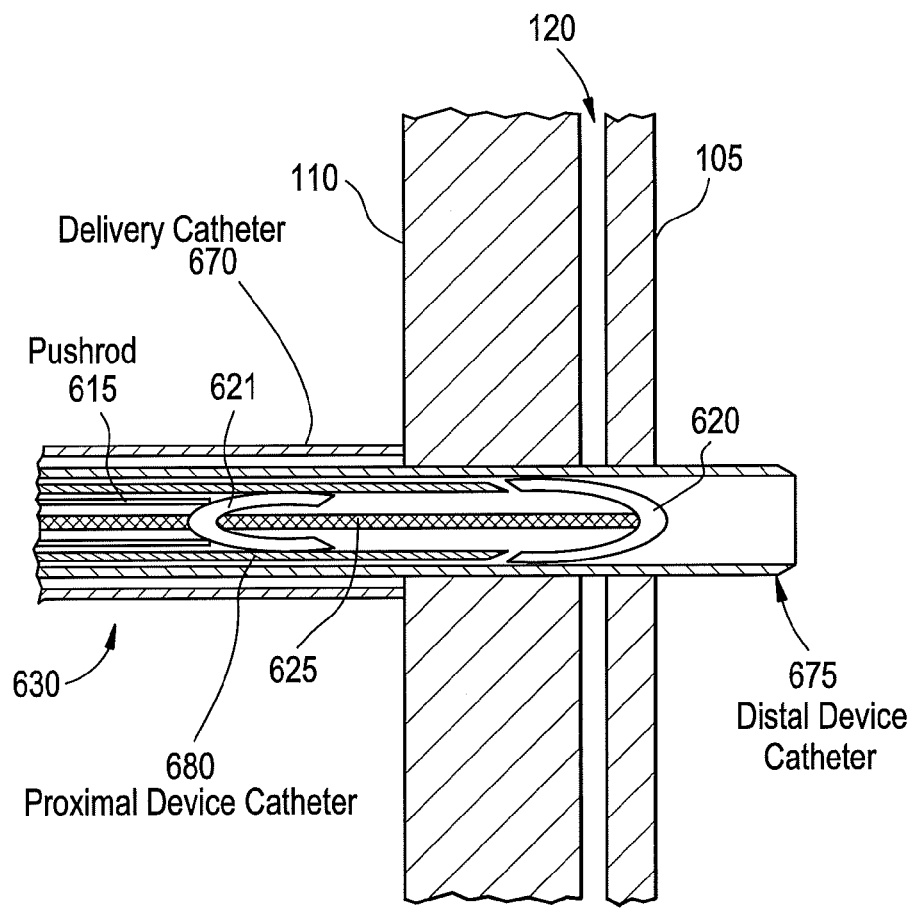
FIG. 12 is a perspective view showing the relationship between components comprising the deployment device and closure device after the needle retracted and the proximal device catheter, closure device and plunger are back-loaded into the distal end of the distal device catheter.

After the needle 605 has penetrated the septum primum 105 and septum secundum 110 into the left atrium, the needle 605 is retracted from the distal device catheter 675 (and thus the delivery catheter 670) and replaced with a proximal device catheter 680. The distal device catheter 675 remains in place. The proximal device catheter has the closure device 600, including the proximal and distal anchors 621, 620 and closure line 625 loaded within its distal end. A plunger 615 may also be coaxially disposed and slideably engaged within the proximal catheter 680 to assist in deploying the closure device 600. FIG. 12 is a section view of the closure device and proximal device catheter 680 loaded into the distal end of the distal device catheter 675.

Figure 13:
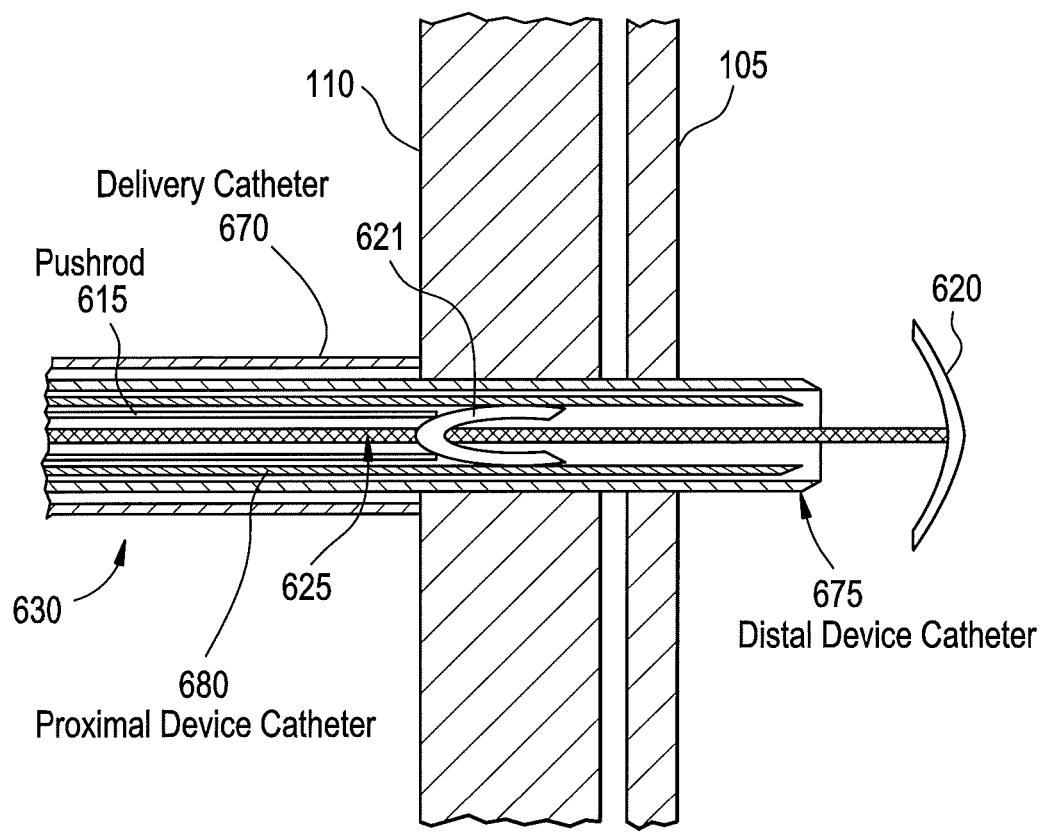
FIG. 13 is a perspective view showing the relationship between components comprising the deployment device and closure device after the proximal device catheter is advanced along the distal device catheter and deploys the distal anchor 620, according to one embodiment of the present invention.

The anchor 620 is deployed into the left atrium by holding delivery catheter 670 and distal device catheter 675 steady, and distally advancing the proximal device catheter 680 and plunger 615. During deployment, the proximal device catheter 680 pushes against the back portion of anchor 620 until anchor 620 is advanced from the distal end of the distal device catheter 675. The movement of anchor 620 necessarily translates, through closure line 625, to movement of anchor 621. As anchor 620 enters the right atrium the shape memory material properties allow the anchor 620 to assume it unconstrained shape. FIG. 13 illustrates the anchor 620 deployed from the needle 605 by the plunger 615 according to one embodiment of the present invention.

Figure 14:
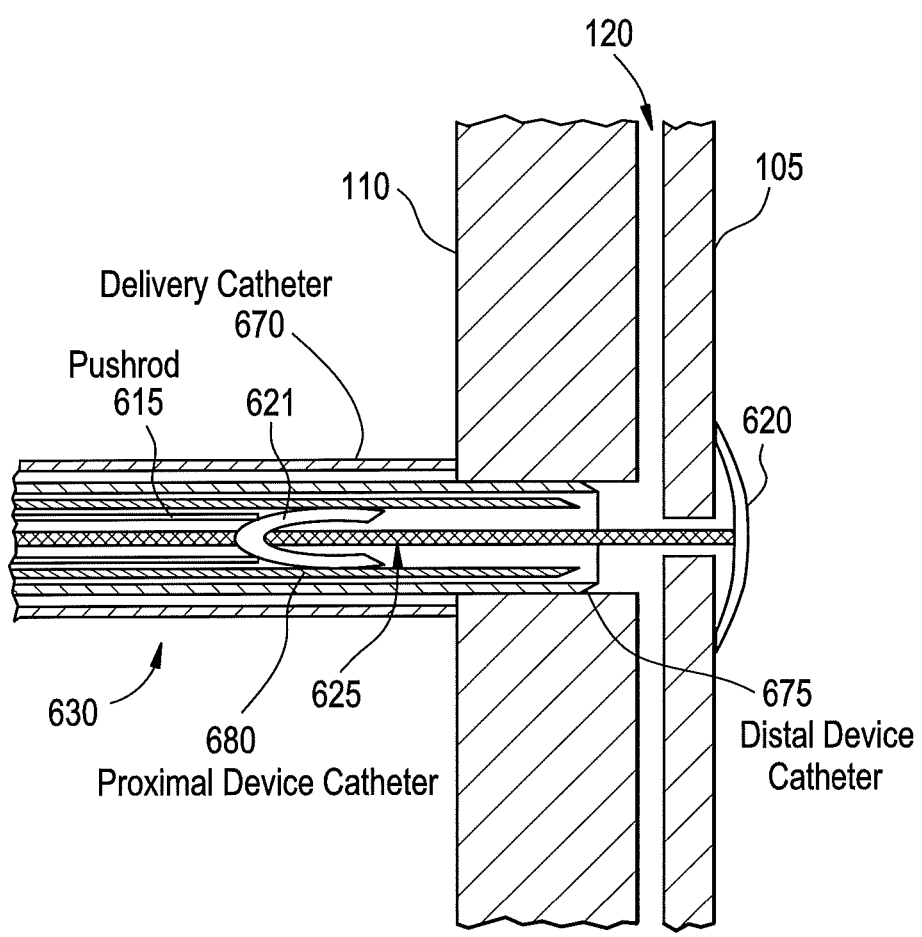
FIG. 14 is a perspective view showing the relationship between components comprising the deployment device and closure device after the proximal and distal device catheters are partially retracted back through the delivery catheter, according to one embodiment of the present invention.

Once the distal anchor 620 is released from the distal device catheter 675, the proximal and distal device catheters 680, 675 can be slowly retracted through the delivery catheter 670. This retraction causes tension in the closure line 625, and caused the distal anchor 620 to seat against the septum primum 105. FIG. 14 illustrated the partial retraction of the proximal and distal device catheters 680, 675 and seating of the distal anchor 620 according to one embodiment of the present invention.

It should be noted that in some embodiments, friction between the coaxially oriented members is such that retraction of the distal device catheter 675 will necessarily cause the simultaneous retraction of the proximal device catheter 680 and plunger 615.

Figure 15:
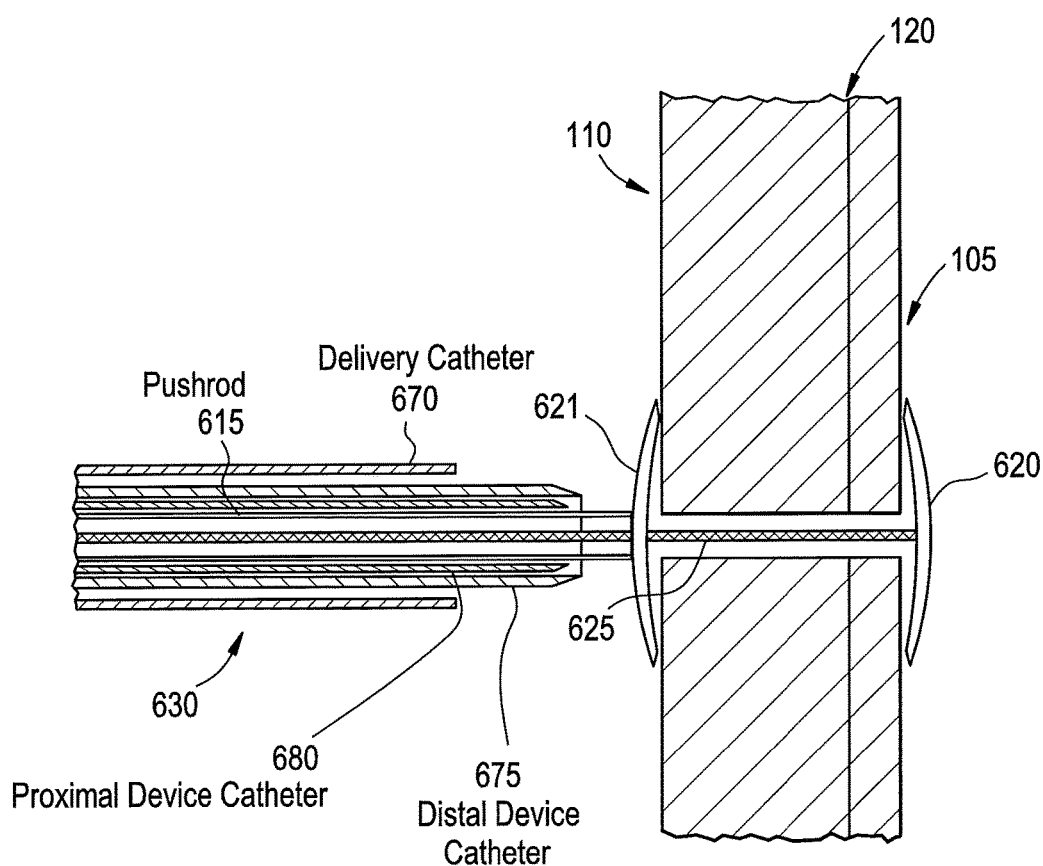
FIG. 15 is a perspective view showing the relationship between components comprising the deployment device and closure device after the delivery catheter, proximal device catheter and distal device catheter are partially retracted and the plunger advanced to deploy the proximal anchor, according to one embodiment of the present invention.

Once the proximal and distal device catheters 680, 675 are withdrawn far enough the clear the septum primum 105 and septum secundum 110 respectively, the plunger 615 may be used to deploy the anchor 621 to the fully unrestrained shape. FIG. 15 is a section view illustrating the plunger 615 deploying the proximal anchor 621 from the distal end of the proximal and distal device catheters 680, 675. If necessary, anchor 621 may be slid toward anchor 620 along closure line 625 until sufficient relative proximation is achieved between septum primum 105 and septum secundum 110. Any unwanted length of closure line 625 that remains unconstrained within the right atrium may be mechanically removed. Devices known in the art capable of removing the excess closure line 625 include catheter-based snare and cut devices. In addition to independent devices, a mechanical cut and removal mechanism may be integrated into the deployment device 630.

The closure device will then be in position, with the anchor 621 opened against the septum secundum 110, and the closure line 625 connecting the anchors 620, 621 through the septum primum 105 and septum secundum 110, holding the septum primum 105 in place.

Figure 16:
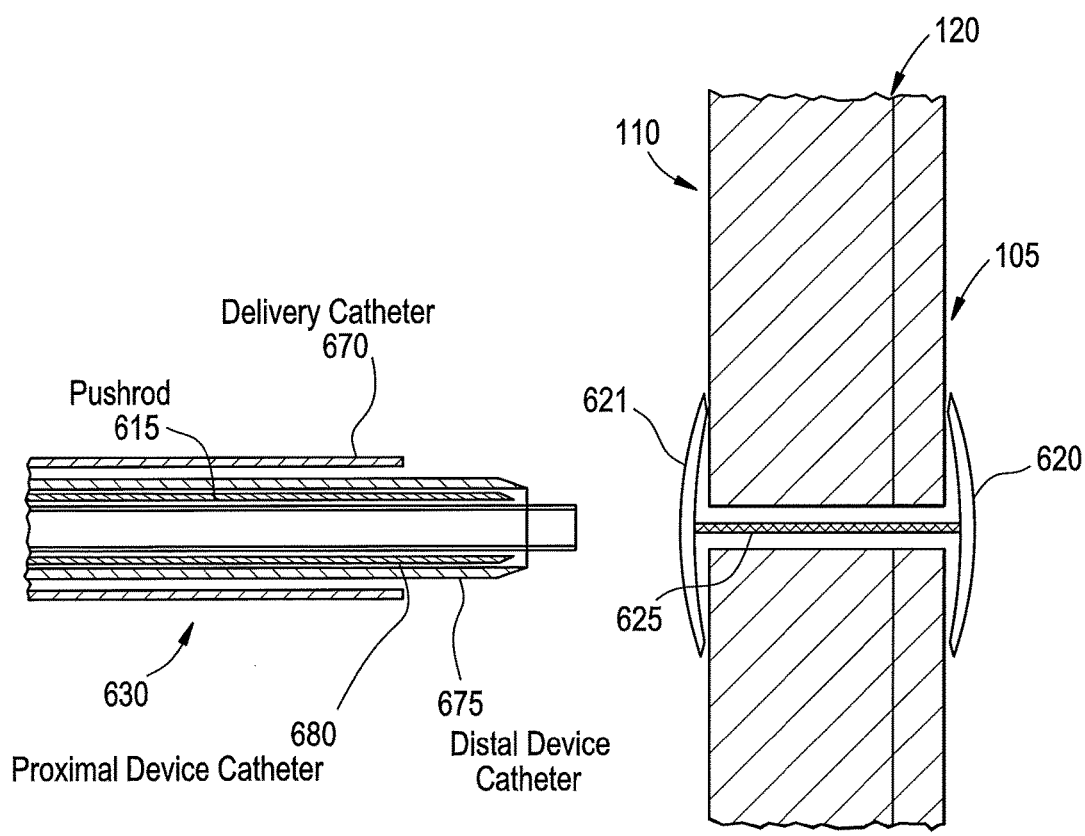
FIG. 16 is a perspective view showing the relationship between components comprising the deployment device and closure device after the closure device is fully deployed, according to one embodiment of the present invention.

FIG. 16 illustrates the closure device 600 in the fully deployed position.

Figure 17:
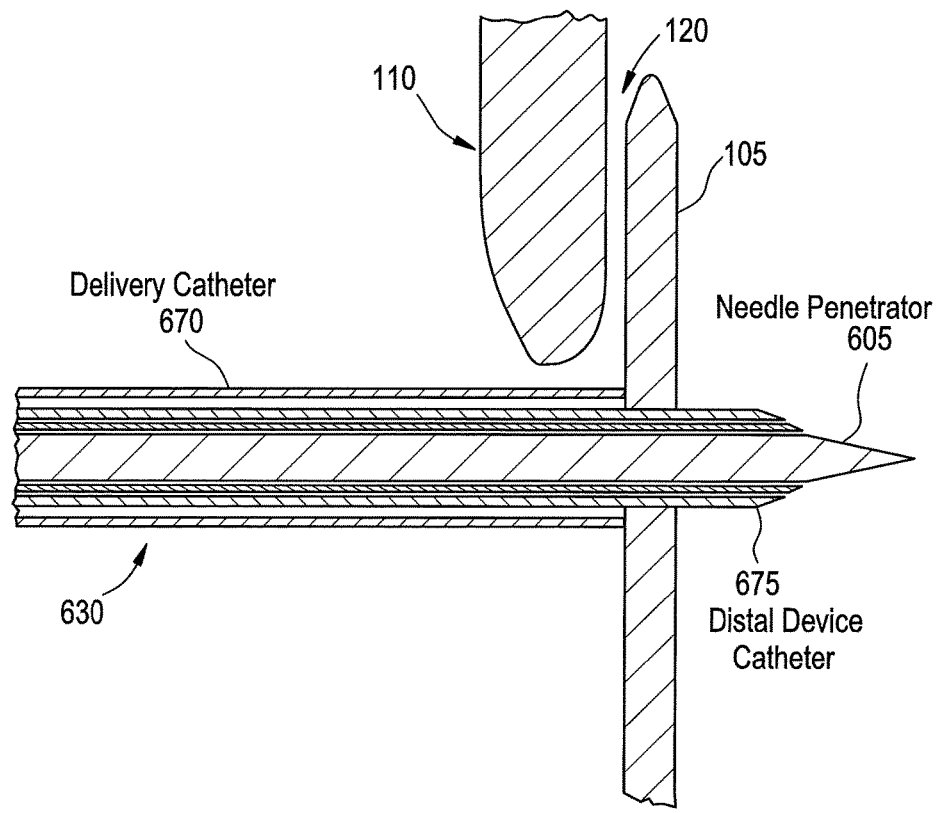
FIG. 17 is a perspective view showing the relationship between components comprising the deployment device and closure device after the needle punctures through the septum primum into the left atrium, according to one embodiment of the present invention.

As noted previously, certain anatomical features of the atrial chambers and atrial septum may allow adequate closure of the PFO to be made through only the septum secundum 110 or septum primum 105. FIGS. 17 though 22 are section views illustrating the method steps for deploying the closure device 600 through the septum primum 105 only, and achieve proximation between the septum primum 105 and septum secundum 110, according to one embodiment of the present invention.

By way of example, once in the right atrium, the distal tip of the guiding catheter is positioned against the septum primum 105 in the intra-atrial septal wall. The needle 605 is then advanced distally through the distal device catheter 675 until the needle 605 punctures through the septum primum 105 into the left atrium. The configuration of the deployment device 630, including the needle 605 and distal device catheter 675 puncturing through the septum secundum 110 and septum primum 105 is shown in FIG. 17.

Figure 18:
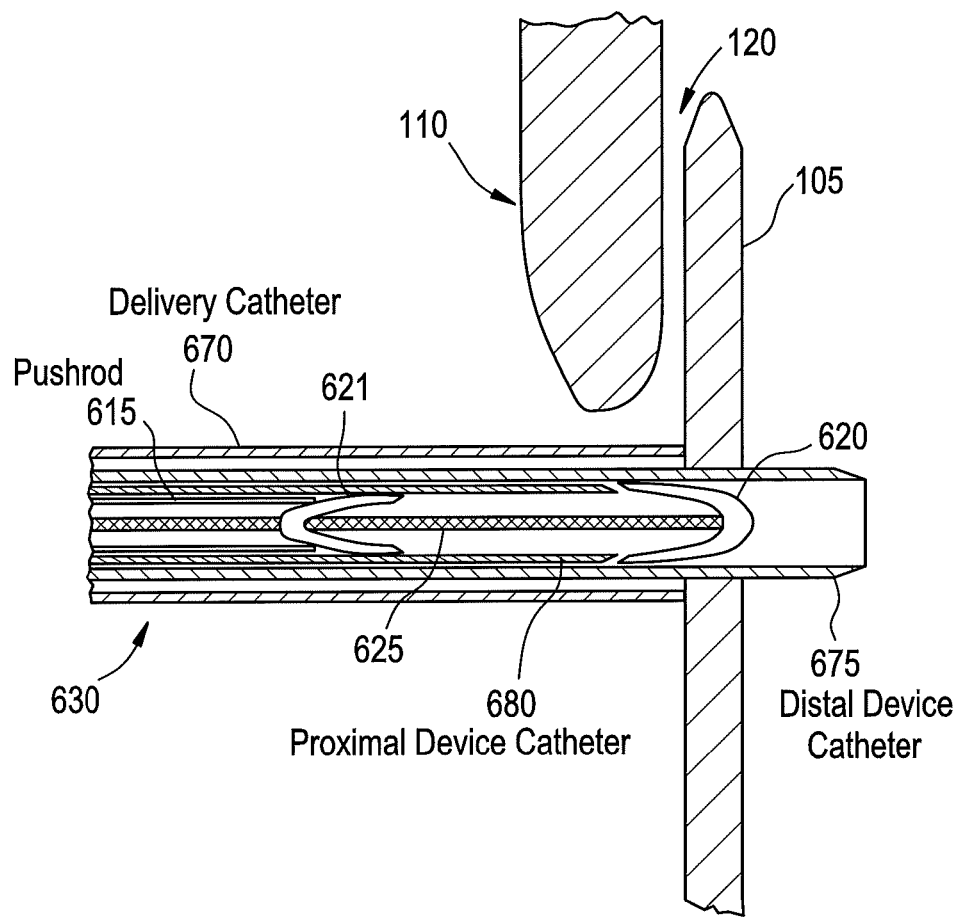
FIG. 18 is a perspective view showing the relationship between components comprising the deployment device and closure device after the needle retracted and the proximal device catheter, closure device and plunger are back-loaded into the distal end of the distal device catheter.

After the needle 605 has penetrated the septum primum 105 into the left atrium, the needle 605 is retracted from the distal device catheter 675 (and thus the delivery catheter 670) and replaced with a proximal device catheter 680, which is back-loaded into the distal device catheter and advanced to its distal end. The distal device catheter 675 remains in place. The proximal device catheter has the closure device 600, including the proximal and distal anchors 621, 620 and closure line 625 loaded within its distal end. A plunger 615 may also be coaxially disposed and slideably engaged within the proximal catheter 680 to assist in deploying the closure device 600. FIG. 18 is a section view of the closure device and proximal device catheter 680 loaded into the distal end of the distal device catheter 675.

Figure 19:
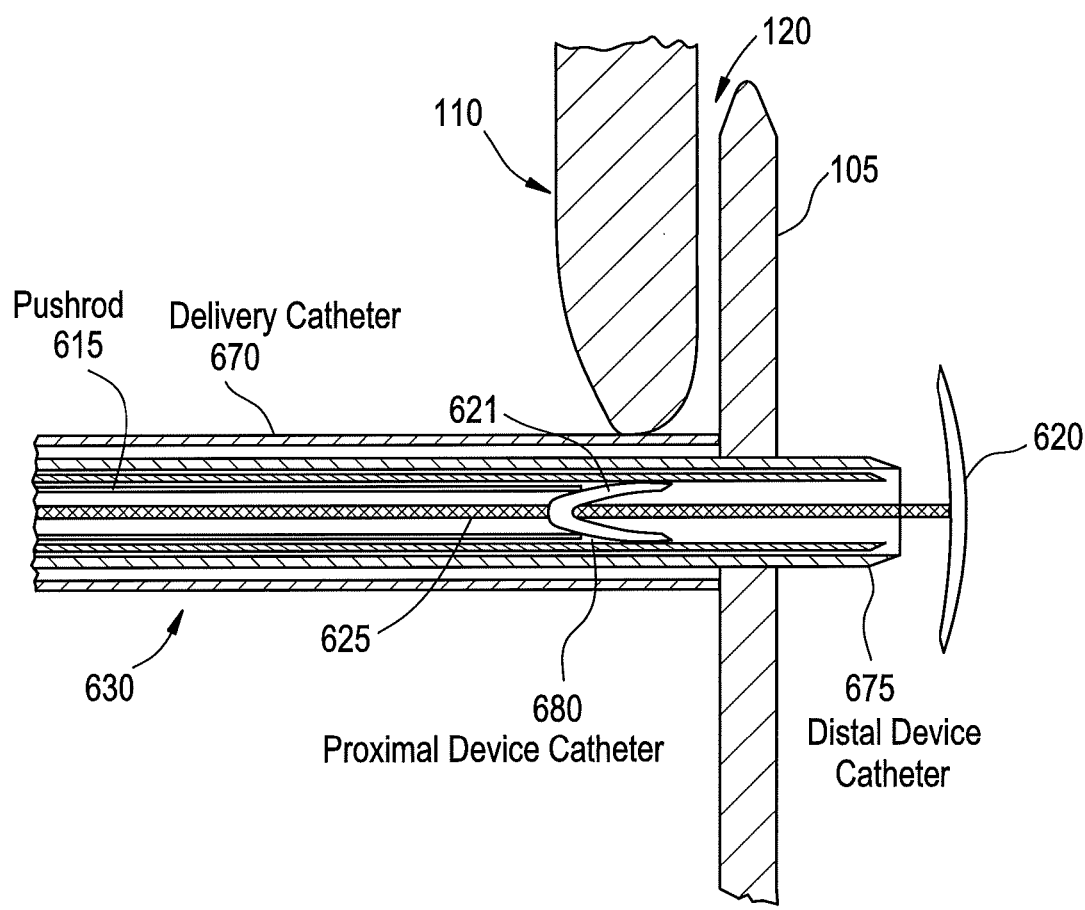
FIG. 19 is a perspective view showing the relationship between components comprising the deployment device and closure device after the proximal device catheter is advanced along the distal device catheter and deploys the distal anchor 620, according to one embodiment of the present invention.

The anchor 620 is deployed into the left atrium by holding delivery catheter 670 and distal device catheter 675 steady, and distally advancing the proximal device catheter 680 and plunger 615. During deployment, the proximal device catheter 680 pushes against the back portion of anchor 620 until anchor 620 is advanced from the distal end of the distal device catheter 675. The movement of anchor 620 necessarily translates, through closure line 625, to movement of anchor 621. As anchor 620 enters the right atrium the shape memory material properties allow the anchor 620 to assume it unconstrained shape. FIG. 19 illustrates the anchor 620 deployed from the needle 605 by the plunger 615 according to one embodiment of the present invention.

Figure 20:
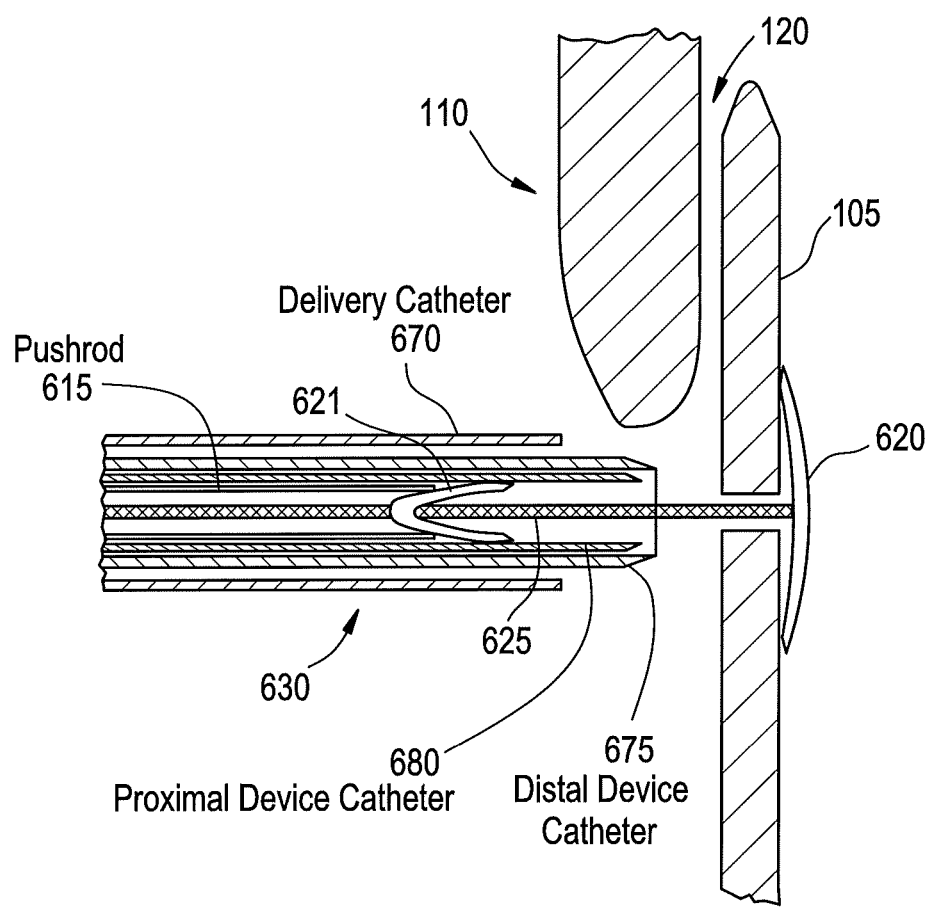
FIG. 20 is a perspective view showing the relationship between components comprising the deployment device and closure device after the proximal and distal device catheters are partially retracted back through the delivery catheter, according to one embodiment of the present invention.

Once the distal anchor 620 is released from the distal device catheter 675, the proximal and distal device catheters 680, 675 can be slowly retracted through the delivery catheter 670. This retraction causes tension in the closure line 625, and caused the distal anchor 620 to seat against the septum primum 105. FIG. 20 illustrated the partial retraction of the proximal and distal device catheters 680, 675 and seating of the distal anchor 620 according to one embodiment of the present invention.

It should be noted that in some embodiments, friction between the coaxially oriented members is such that retraction of the distal device catheter 675 will necessarily cause the simultaneous retraction of the proximal device catheter 680 and plunger 615.

Figure 21:
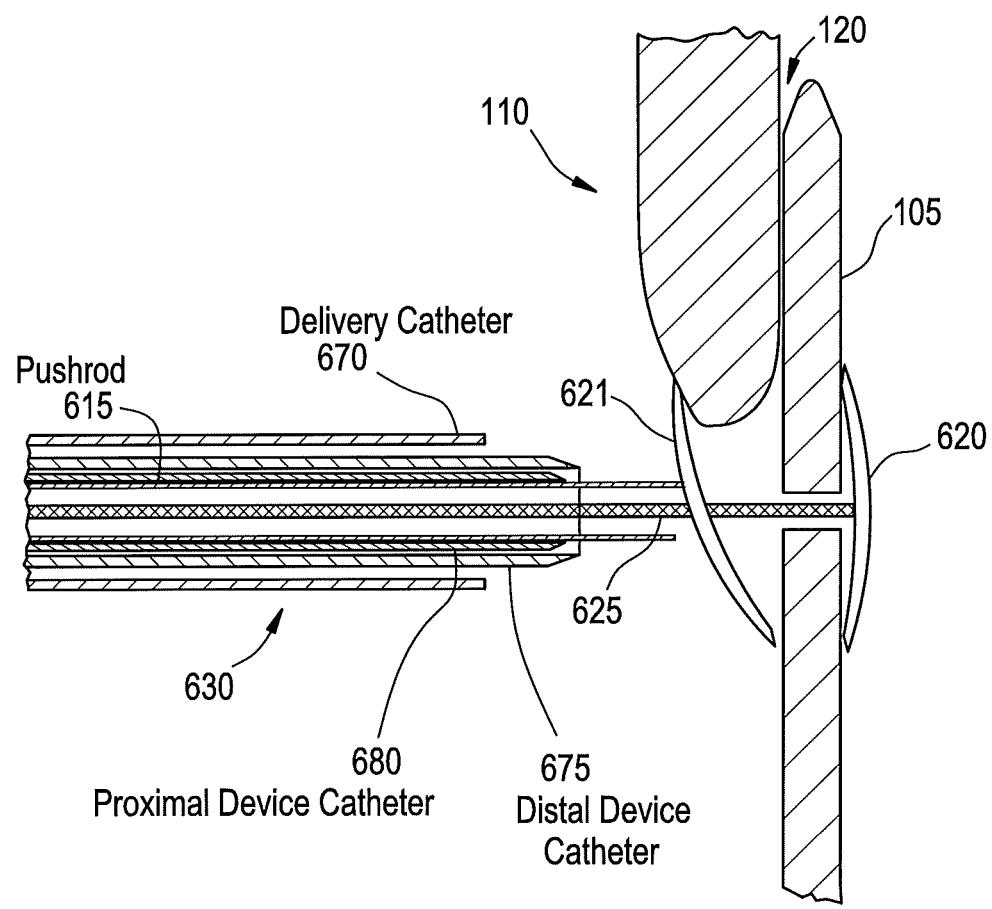
FIG. 21 is a perspective view showing the relationship between components comprising the deployment device and closure device after the delivery catheter, proximal device catheter and distal device catheter are partially retracted and the plunger advanced to deploy the proximal anchor, according to one embodiment of the present invention.

Once the proximal and distal device catheters 680, 675 are withdrawn far enough the clear the septum primum 105, the plunder 615 may be used to deploy the anchor 621 to the fully unrestrained shape. FIG. 21 is a section view illustrating the plunger 615 deploying the proximal anchor 621 from the distal end of the proximal and distal device catheters 680, 675. It should be noted that proximal anchor 621 is of sufficient size and shape to seat against the septum primum 105 and septum secundum 110. If necessary, anchor 621 may be slid toward anchor 620 along closure line 625 until sufficient relative proximation is achieved between septum primum 105 and septum secundum 110. Any unwanted length of closure line 625 that remains unconstrained within the right atrium may be mechanically removed. Devices known in the art capable of removing the excess closure line 625 include catheter-based snare and cut devices. In addition to independent devices, a mechanical cut and removal mechanism may be integrated into the deployment device 630.

The closure device will then be in position, with the anchor 621 opened against the septum secundum 110, and the closure line 625 connecting the anchors 620, 621 through the septum primum 105 and septum secundum 110, holding the septum primum 105 in place.

Figure 22:
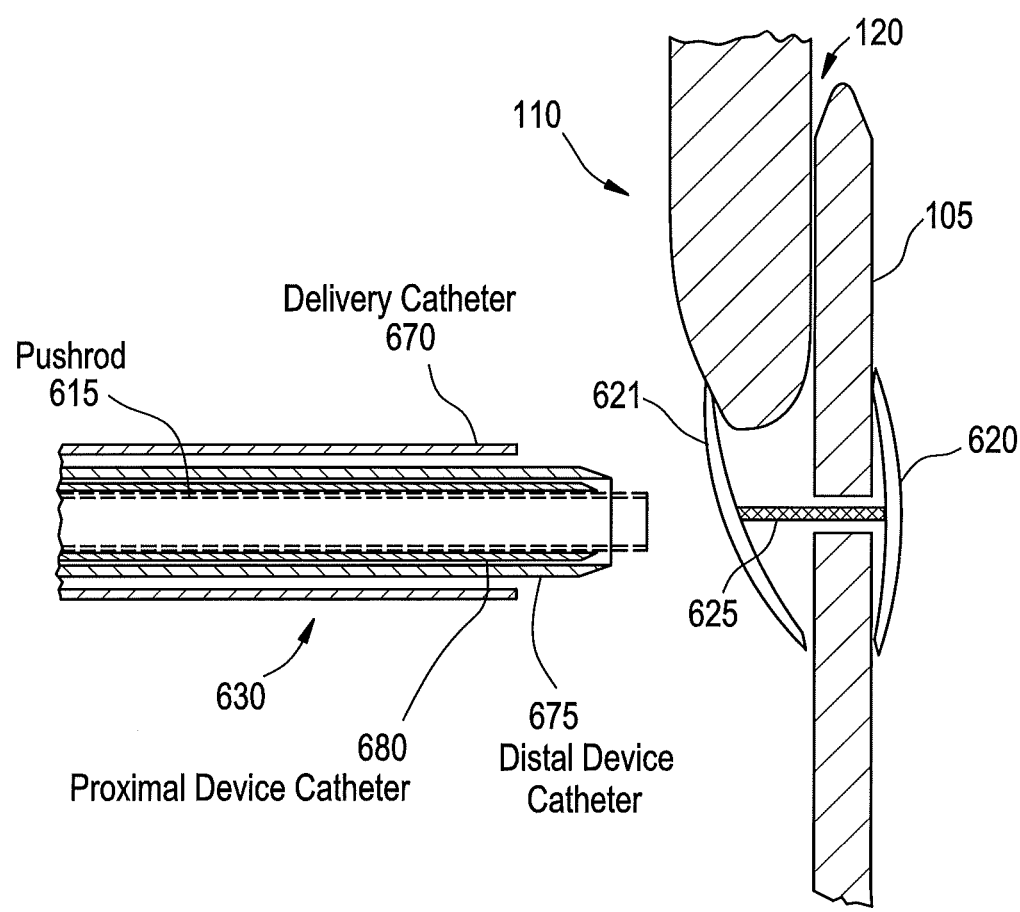
FIG. 22 is a perspective view showing the relationship between components comprising the deployment device and closure device after the closure device is fully deployed, according to one embodiment of the present invention.

FIG. 22 illustrates the closure device 600 in the fully deployed position.

These and other objects and advantages of this invention will become obvious to a person of ordinary skill in this art upon reading of the detailed description of this invention including the associated drawings.

Various other modifications, adaptations, and alternative designs are of course possible in light of the above teachings. Therefore, it should be understood at this time that within the scope of the appended claims the invention might be practiced otherwise than as specifically described herein.

What is claimed is:

1. A method to facilitate closure of a PFO in a heart, the heart having an interatrial septum comprised of a septum primum and a septum secundum between a first atrium and a second atrium, the method comprising:

introducing a mechanical closure device into the first atrium of the heart, the closure device having a proximal end portion and a distal end portion, and further comprising a flexible closure line coupled to a proximal expandable anchor and a distal expandable anchor, the proximal and distal expandable anchors each having a plurality of longitudinally oriented legs attached between proximal and distal end rings, the proximal and distal end rings being held in a longitudinally extended constrained position by a constraining force;

penetrating only the septum primum or the septum secundum from the first atrium to the second atrium in the heart at a first location along the interatrial septum so that at least the distal end portion of the closure device is located in the second atrium;

deploying the distal expandable anchor associated with the closure device into the second atrium by distally advancing a catheter to push against a back portion of the distal expandable anchor to distally advance the distal expandable anchor and releasing the constraining force, allowing the legs of the distal expandable anchor to expand radially outward, causing the proximal and distal end rings of the distal expandable anchor to move longitudinally inward towards one another;

partially withdrawing the closure device from the second atrium to the first atrium;

deploying the proximal expandable anchor associated with the closure device into the first atrium by distally advancing a plunger within the catheter to push and distally advance the proximal expandable anchor and releasing the constraining force, allowing the legs of the proximal expandable anchor to expand radially outward, causing the proximal and distal end rings of the proximal expandable anchor to move longitudinally inward towards one another; and radially expanding the proximal and distal expandable anchors into a flat shape by tensioning the closure line.

2. The method of claim 1 wherein introducing the mechanical closure device into an atrium of the heart comprises a minimally invasive procedure.

3. The method of claim 2 wherein the minimally invasive procedure is a percutaneous procedure.

4. The method of claim 1 wherein penetrating the interatrial septum comprises piercing the interatrial septum.

5. The method of claim 1 wherein penetrating the interatrial septum comprises non-core cutting of the interatrial septum.

6. The method of claim 1 further comprising adjusting the proximal anchor relative to the distal anchor to enhance proximation.

7. The method of claim 6 wherein adjusting the proximal anchor comprises uni-axially adjusting the proximal anchor relative to the closure line associated with the closure device.

8. The method of claim 7 wherein uni-axially adjusting the proximal anchor comprises incrementally adjusting the proximal anchor relative to the closure line associated with the closure device.

9. The method of claim 1 further comprising assessing the degree of proximation between the septum secundum and septum primum.

10. The method of claim 1 further comprising releasing the closure device from a delivery device.

* * * * *